United States Patent
Jiang et al.

(10) Patent No.: US 9,724,383 B2
(45) Date of Patent: Aug. 8, 2017

(54) STABILIZED TRIMERIC HIV-1 GP41 FUSION INHIBITOR POLYPEPTIDES COMPRISING THE N-TERMINAL HEPTAD REPEAT (NHR) AND FOLDON (FD) TRIMERIZATION MOTIF

(71) Applicant: New York Blood Center, Inc., New York, NY (US)

(72) Inventors: Shibo Jiang, New York, NY (US); Zhi Qi, Corona, NY (US); Xi Chen, Elmhurst, NY (US); Chungen Pan, Guangdong Province (CN)

(73) Assignee: New York Blood Center, Inc., New York, NY (US)

( * ) Notice: Subject to any disclaimer, the term of this patent is extended or adjusted under 35 U.S.C. 154(b) by 13 days.

(21) Appl. No.: 14/796,725

(22) Filed: Jul. 10, 2015

(65) Prior Publication Data
US 2015/0306174 A1 Oct. 29, 2015

Related U.S. Application Data

(62) Division of application No. 12/702,209, filed on Feb. 8, 2010, now Pat. No. 9,115,186.

(60) Provisional application No. 61/151,110, filed on Feb. 9, 2009.

(51) Int. Cl.
| | | |
|---|---|---|
| *C07K 14/05* | (2006.01) | |
| *A61K 38/16* | (2006.01) | |
| *C07K 14/005* | (2006.01) | |
| *C12N 7/00* | (2006.01) | |
| *A61K 38/00* | (2006.01) | |

(52) U.S. Cl.
CPC .......... *A61K 38/162* (2013.01); *C07K 14/005* (2013.01); *C12N 7/00* (2013.01); *A61K 38/00* (2013.01); *C07K 2319/735* (2013.01); *C12N 2740/16022* (2013.01); *C12N 2740/16033* (2013.01); *C12N 2740/16111* (2013.01); *C12N 2740/16122* (2013.01)

(58) Field of Classification Search
CPC ........ A61K 38/162; A61K 38/00; C12N 7/00; C12N 2740/16122; C07K 14/005; C07K 2319/735
See application file for complete search history.

(56) References Cited

U.S. PATENT DOCUMENTS

| 5,444,044 A | 8/1995 | Jiang et al. |
| 2004/0044183 A1 | 3/2004 | Eckert |
| 2005/0106177 A1 | 5/2005 | Sodroski |
| 2010/0098724 A1 | 4/2010 | Jiang |

FOREIGN PATENT DOCUMENTS

| WO | 2004/104033 | 12/2004 |
| WO | 2005/007831 | 1/2005 |
| WO | 2006/038131 | 4/2006 |
| WO | 2006/105199 | 10/2006 |
| WO | 2008/019817 | 2/2008 |
| WO | 2010/045613 | 4/2010 |

OTHER PUBLICATIONS

Gait, M. J., and J. Karn, 1995, Progress in anti-HIV structure-based drug design, TIBTECH 13:430-438.*
Root, M. J., and H. K. Steger, 2004, HIV-1 gp41 as a Target for Viral Entry Inhibition, Curr. Pharm. Design 10:1805-1825.*
Bellamy et al. "Functional links between the fusion peptide-proximal polar segment and membrane-proximal region of human immunodeficiency virus gp41 in distinct phases of membrane fusion." J Biol Chem 282: 23104-23116, 2007.
Chan et al. "Evidence that a prominent cavity in the coiled coil of HIV type 1 gp41 is an attractive drug target." Proc Natl Acad Sci USA 95: 15613-15617, 1998.
Chan et al. "Core structure of gp41 from the HIV envelope glycoprotein." Cell 89: 263-273, 1997.
Chan et al. "HIV entry and its inhibition." Cell 93: 681-684, 1998.
Dervillex et al. "Stable expression of soluble therapeutic peptides in eukaryotic cells by multimerisation: application to the HIV-1 fusion inhibitory peptide C46." ChemMedChem 1: 330-339, 2006.
D.M. Eckert et al., "Design of potent inhibitors of HIV-1 entry from the gp41 N-peptide region," 98(20) Proc. Natl. Acad. Sci. USA 11187 (2001).
Farzan et al. "Stabilization of human immunodeficiency virus type 1 envelope glycoprotein trimers by disulfide bonds introduced into the gp41 glycoprotein ectodomain." J. Virol. 72:7620-7625, 1998.
He et al. "Identification of a critical motif for the human immunodeficiency virus type 1 (HIV-1) gp41 core structure: implications for designing novel anti-HIV fusion inhibitors." J. Virol. 82:6349-6358, 2008.
Jiang et al. "N-substituted pyrrole derivatives as novel human immunodeficiency virus type 1 entry inhibitors that interfere with the gp41 six-helix bundle formation and block virus fusion." Antimicrob Agents Chemother 48: 1349-4359, 2004.
Jiang et al. "HIV-1 inhibition by a peptide." Nature 365: 113, 1993.
Jiang et al. "Effect of Amino Acid Replacements, Additions and Deletions on the Antiviral Activity of a Peptide Derived from the HIV-1 GP41 Sequence." Peptide Research, vol. 8, No. 6, 1995.
Lawless et al. "HIV-1 Membrane Fusion Mechanism: Structural Studies of the Interactions between Biologically-Active Peptides from gp41." Biochemistry 1996, 35, 13697-13708.

(Continued)

*Primary Examiner* — Jeffrey Parkin
(74) *Attorney, Agent, or Firm* — K&L Gates LLP; Louis C. Cullman; Michelle Glasky Bergman

(57) ABSTRACT

Disclosed herein are trimeric polypeptide pharmaceutical compositions comprising three monomers, each monomer comprising a polypeptide having the amino acid sequence of the N-terminal heptad repeat (NHR or HR1) or C-terminal heptad repeat (CHR or HR2) of the transmembrane glycoprotein of human immunodeficiency virus (HIV) and a trimerization motif.

4 Claims, 10 Drawing Sheets

(56) References Cited

OTHER PUBLICATIONS

Liu et al. (2005) Different from the HIV fusion inhibitor C34, the anti-HIV drug Fuzeon (T-20) inhibits HIV-1 entry by targeting multiple sites in gp41 and gp120. J Biol Chem 280: 11259-11273.
Liu et al. "HIV Entry Inhibitors Targeting gp41: From Polypeptides to Small-Molecule Compounds." Current Pharmaceutical Design, vol. 13, No. 2, 2007, pp. 143-162.
Liu et al. "HIV gp41 C-terminal heptad repeat contains multifunctional domains." J. Bio. Chem. 282:9612-9620, 2007.
Louis et al. "Covalent Trimers of the Internal N-Terminal Trimeric Coiled-Coil of gp41 and Antibodies Directed Against them are Potent Inhibitors of HIV envelope-mediated Cell Fusion." Journal of Biological Chemistry, vol. 278, No. 22, 2003, pp. 20278-20285.
Louis et al. "Design and Properties of Nccg-gp41, a chimeric pg41 molecule with nanomolar HIV fusion inhibitory activity." J. Biol. Chem. 276:29485-29489, 2001.
Lu et al. "Automatic quantitation of HIV-1 mediated cell-to-cell fusion with a digital image analysis system (DIAS): application for rapid screening of HIV-1 fusion inhibitors." J Virol Methods 107: 155-161, 2003.
Lu et al. "A trimeric structural domain of the HIV-1 transmembrane glycoprotein." Nat Struct Biol 2: 1075-1082, 1995.
Nelson et al. "Antibody elicited against the pg41 N-heptad repeat (NHR) coiled-coil can neutralize HIV-1 with modest potency but non-neutralizing antibodies also bind to NHR mimetics." Virology 277:170-183, 2008.
Neurath et al. "Anti-HIV-1 activity of cellulose acetate phthalate: synergy with soluble CD4 and induction of "dead-end" gp41 six-helix bundles." BMC Infect Dis 2: 6, 2002.
Qi et al. "Rationally designed anti-HIV peptides containing multifunctional domains as molecule probes for studying the mechanisms of action of the first and second generation HIV fusion inhibitors." J. Bio. Chem. 283:30376-30384, 2008.

Reeves et al. "Impact of mutations in the coreceptor binding site on human immunodeficiency virus type 1 fusion, infection, and entry inhibitor sensitivity." J Virol 78: 5476-5485, 2004.
Rimsky et al. "Determinants of Human Immunodeficiency Virus Type 1 Resistance to gp41-Derived Inhibitory Peptides." Journal of Virology, 1998, vol. 72, No. 2, p. 986-993.
Tam et al. "A Facile Ligation Approach to Prepare Three-Helix Bundles of HIV Fusion-State Protein Mimetics." Organic Letters, 2002, vol. 4, No. 23, 4167-4170.
Weissenhorn et al. "Atomic Structure of the Ectodomain from HIV-1 gp41." Nature 387: 426-428, 1997.
Wexler-Cohen et al. "Demonstrating the C-terminal boundary of the HIV 1 fusion conformation in a dynamic ongoing fusion process and implication for fusion inhibition." FASEB J 21: 3677-3684, 2007.
Wexler-Cohen et al. "Structurally Altered Peptides Reveal an Important Role for N-Terminal Heptad Repeat Binding and Stability in the Inhibitory Action of HIV-1 Peptode DP178." The Journal of Biological Chemistry, vol. 281, No. 14, pp. 9005-9010, 2006.
Wild et al. "The inhibitory activity of an HIV type 1 peptide correlates with its ability to interact with a leucine zipper structure." AIDS Res Hum Retroviruses, Mar. 11, 1995(3):323-5.
Wild et al. "Peptides corresponding to a predictive a-helical domain of human immunodeficiency virus type 1 gp41 are potent inhibitors of virus infection." Proc. Natl. Acad. Sci. vol. 91, pp. 9770-9774, 1994.
Wild "Supporting Basic Research: Discovering a New Class of Anti-HIV Drug." AIDS Patient Care and STDs, vol. 20 No. 7, 2006.
Yang et al. "Highly Stable Trimers Formed by Human Immunodeficiency Virus Type 1 Envelope Glycoproteins Fused with the Trimeric Motif of T4 Bacteriophage Fibritin." Journal of Virology, vol. 76, No. 9m 2002, p. 4634-4642.
Stetefeld, J., et al., 2003, Collagen stabilization at atomic level: crystal structure of designed (GlyProPro)10foldon, Structure 11:339-346.

* cited by examiner

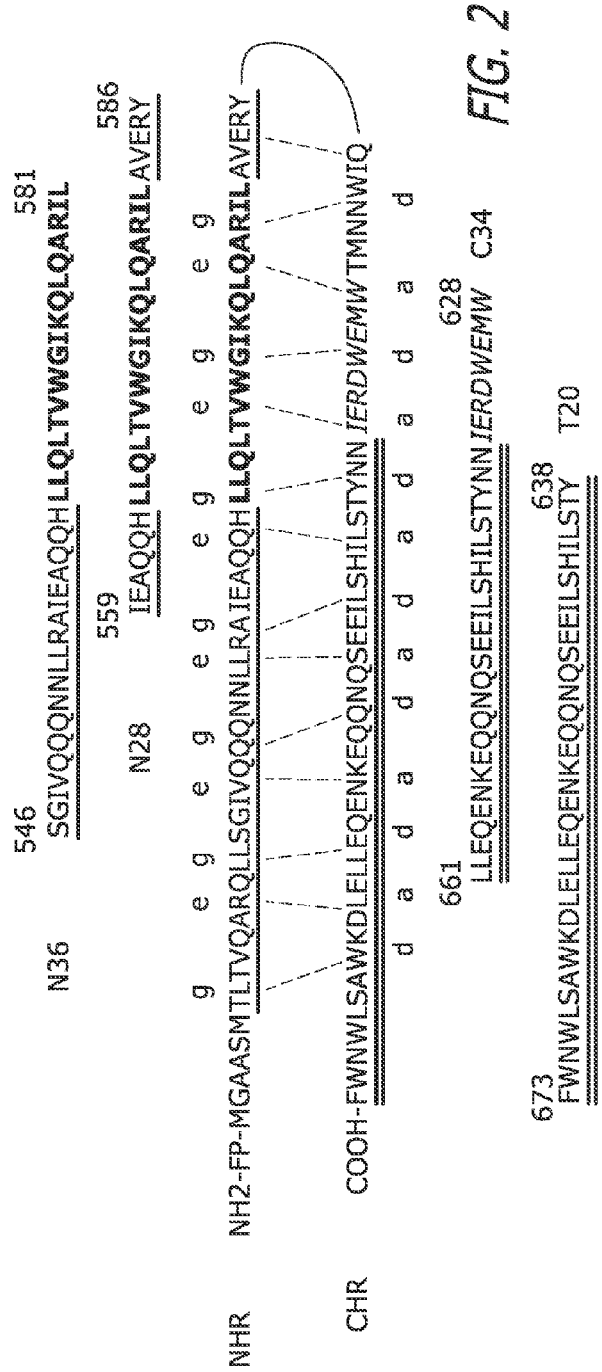
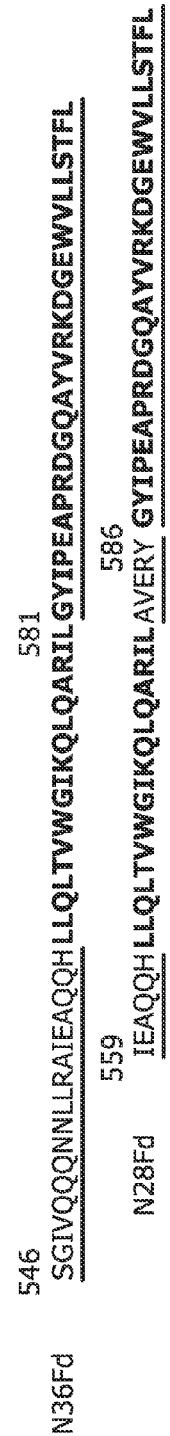
FIG. 2
FIG. 3

SEQUENCE LISTING

```
<160> NUMBER OF SEQ ID NOS: 37

<210> SEQ ID NO 1
<211> LENGTH: 63
<212> TYPE: PRT
<213> ORGANISM: Artificial Sequence
<220> FEATURE:
<223> OTHER INFORMATION: N36-Fd1 peptide

<400> SEQUENCE: 1

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu Gly Tyr Ile Pro Glu Ala Pro Arg Asp Gly Gln Ala
        35                  40                  45

Tyr Val Arg Lys Asp Gly Glu Trp Val Leu Leu Ser Thr Phe Leu
    50                  55                  60

<210> SEQ ID NO 2
<211> LENGTH: 73
<212> TYPE: PRT
<213> ORGANISM: Artificial Sequence
<220> FEATURE:
<223> OTHER INFORMATION: N46-Fd1 peptide

<400> SEQUENCE: 2

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln Gln His Leu Leu Gln
            20                  25                  30

Leu Thr Val Trp Gly Ile Lys Gln Leu Gln Ala Arg Ile Leu Gly Tyr
        35                  40                  45

Ile Pro Glu Ala Pro Arg Asp Gly Gln Ala Tyr Val Arg Lys Asp Gly
    50                  55                  60

Glu Trp Val Leu Leu Ser Thr Phe Leu
65                  70

<210> SEQ ID NO 3
<211> LENGTH: 78
<212> TYPE: PRT
<213> ORGANISM: Artificial Sequence
<220> FEATURE:
<223> OTHER INFORMATION: N51-Fd1 peptide

<400> SEQUENCE: 3
```

```
Gln Ala Arg Gln Leu Leu Ser Gly Ile Val Gln Gln Asn Asn Leu
1               5                   10                  15

Leu Arg Ala Ile Glu Ala Gln Gln His Leu Leu Gln Leu Thr Val Trp
                20                  25                  30

Gly Ile Lys Gln Leu Gln Ala Arg Ile Leu Ala Val Glu Arg Tyr Leu
            35                  40                  45

Lys Gln Gln Gly Tyr Ile Pro Glu Ala Pro Arg Asp Gly Gln Ala Tyr
    50                  55                  60

Val Arg Lys Asp Gly Glu Trp Val Leu Leu Ser Thr Phe Leu
65              70                  75
```

<210> SEQ ID NO 4
<211> LENGTH: 81
<212> TYPE: PRT
<213> ORGANISM: Artificial Sequence
<220> FEATURE:
<223> OTHER INFORMATION: N54-Fd1 peptide

<400> SEQUENCE: 4

```
Ser Thr Met Gly Ala Ala Ser Met Thr Leu Thr Val Gln Ala Arg Gln
1               5                   10                  15

Leu Leu Ser Gly Ile Val Gln Gln Asn Asn Leu Leu Arg Ala Ile
                20                  25                  30

Glu Ala Gln Gln His Leu Leu Gln Leu Thr Val Trp Gly Ile Lys Gln
            35                  40                  45

Leu Gln Ala Arg Ile Leu Gly Tyr Ile Pro Glu Ala Pro Arg Asp Gly
    50                  55                  60

Gln Ala Tyr Val Arg Lys Asp Gly Glu Trp Val Leu Leu Ser Thr Phe
65              70                  75                  80

Leu
```

<210> SEQ ID NO 5
<211> LENGTH: 87
<212> TYPE: PRT
<213> ORGANISM: Artificial Sequence
<220> FEATURE:
<223> OTHER INFORMATION: N60-Fd1 peptide

<400> SEQUENCE: 5

```
Ser Thr Met Gly Ala Ala Ser Met Thr Leu Thr Val Gln Ala Arg Gln
1               5                   10                  15

Leu Leu Ser Gly Ile Val Gln Gln Gln Asn Asn Leu Leu Arg Ala Ile
                20                  25                  30

Glu Ala Gln Gln His Leu Leu Gln Leu Thr Val Trp Gly Ile Lys Gln
            35                  40                  45

Leu Gln Ala Arg Ile Leu Ala Val Glu Arg Tyr Leu Gly Tyr Ile Pro
    50                  55                  60

Glu Ala Pro Arg Asp Gly Gln Ala Tyr Val Arg Lys Asp Gly Glu Trp
65              70                  75                  80

Val Leu Leu Ser Thr Phe Leu
                85
```

<210> SEQ ID NO 6
<211> LENGTH: 55
<212> TYPE: PRT
<213> ORGANISM: Artificial Sequence
<220> FEATURE:
<223> OTHER INFORMATION: Fd-N28-Fd1 peptide

```
<400> SEQUENCE: 6

Ile Glu Ala Gln Gln His Leu Leu Gln Leu Thr Val Trp Gly Ile Lys
1               5                   10                  15

Gln Leu Gln Ala Arg Ile Leu Ala Val Glu Arg Tyr Gly Tyr Ile Pro
            20                  25                  30

Glu Ala Pro Arg Asp Gly Gln Ala Tyr Val Arg Lys Asp Gly Glu Trp
        35                  40                  45

Val Leu Leu Ser Thr Phe Leu
    50                  55

<210> SEQ ID NO 7
<211> LENGTH: 44
<212> TYPE: PRT
<213> ORGANISM: Artificial Sequence
<220> FEATURE:
<223> OTHER INFORMATION: N17-Fd1 peptide

<400> SEQUENCE: 7

Leu Leu Gln Leu Thr Val Trp Gly Ile Lys Gln Leu Gln Ala Arg Ile
1               5                   10                  15

Leu Gly Tyr Ile Pro Glu Ala Pro Arg Asp Gly Gln Ala Tyr Val Arg
            20                  25                  30

Lys Asp Gly Glu Trp Val Leu Leu Ser Thr Phe Leu
        35                  40

<210> SEQ ID NO 8
<211> LENGTH: 65
<212> TYPE: PRT
<213> ORGANISM: Artificial Sequence
<220> FEATURE:
<223> OTHER INFORMATION: N36-Fd2 peptide

<400> SEQUENCE: 8

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu Gly Ser Gly Tyr Ile Pro Glu Ala Pro Arg Asp Gly
        35                  40                  45

Gln Ala Tyr Val Arg Lys Asp Gly Glu Trp Val Leu Leu Ser Thr Phe
    50                  55                  60

Leu
65

<210> SEQ ID NO 9
<211> LENGTH: 75
<212> TYPE: PRT
<213> ORGANISM: Artificial Sequence
<220> FEATURE:
<223> OTHER INFORMATION: N46-Fd2 peptide

<400> SEQUENCE: 9

Thr Leu Thr Val Gln Ala Arg Gln Leu Leu Ser Gly Ile Val Gln Gln
1               5                   10                  15

Gln Asn Asn Leu Leu Arg Ala Ile Glu Ala Gln His Leu Leu Gln
            20                  25                  30

Leu Thr Val Trp Gly Ile Lys Gln Leu Gln Ala Arg Ile Leu Gly Ser
        35                  40                  45

Gly Tyr Ile Pro Glu Ala Pro Arg Asp Gly Gln Ala Tyr Val Arg Lys
    50                  55                  60
```

```
Asp Gly Glu Trp Val Leu Leu Ser Thr Phe Leu
65                  70                  75
```

<210> SEQ ID NO 10
<211> LENGTH: 80
<212> TYPE: PRT
<213> ORGANISM: Artificial Sequence
<220> FEATURE:
<223> OTHER INFORMATION: N51-Fd2 peptide

<400> SEQUENCE: 10

```
Gln Ala Arg Gln Leu Leu Ser Gly Ile Val Gln Gln Asn Asn Leu
1               5                   10                  15

Leu Arg Ala Ile Glu Ala Gln Gln His Leu Leu Gln Leu Thr Val Trp
                20                  25                  30

Gly Ile Lys Gln Leu Gln Ala Arg Ile Leu Ala Val Glu Arg Tyr Leu
                35                  40                  45

Lys Gln Gln Gly Ser Gly Tyr Ile Pro Glu Ala Pro Arg Asp Gly Gln
            50                  55                  60

Ala Tyr Val Arg Lys Asp Gly Glu Trp Val Leu Leu Ser Thr Phe Leu
65                  70                  75                  80
```

<210> SEQ ID NO 11
<211> LENGTH: 83
<212> TYPE: PRT
<213> ORGANISM: Artificial Sequence
<220> FEATURE:
<223> OTHER INFORMATION: N54-Fd2 peptide

<400> SEQUENCE: 11

```
Ser Thr Met Gly Ala Ala Ser Met Thr Leu Thr Val Gln Ala Arg Gln
1               5                   10                  15

Leu Leu Ser Gly Ile Val Gln Gln Asn Asn Leu Leu Arg Ala Ile
                20                  25                  30

Glu Ala Gln Gln His Leu Leu Gln Leu Thr Val Trp Gly Ile Lys Gln
                35                  40                  45

Leu Gln Ala Arg Ile Leu Gly Ser Gly Tyr Ile Pro Glu Ala Pro Arg
            50                  55                  60

Asp Gly Gln Ala Tyr Val Arg Lys Asp Gly Glu Trp Val Leu Leu Ser
65                  70                  75                  80

Thr Phe Leu
```

<210> SEQ ID NO 12
<211> LENGTH: 89
<212> TYPE: PRT
<213> ORGANISM: Artificial Sequence
<220> FEATURE:
<223> OTHER INFORMATION: N60-Fd2 peptide

<400> SEQUENCE: 12

```
Ser Thr Met Gly Ala Ala Ser Met Thr Leu Thr Val Gln Ala Arg Gln
1               5                   10                  15

Leu Leu Ser Gly Ile Val Gln Gln Asn Asn Leu Leu Arg Ala Ile
                20                  25                  30

Glu Ala Gln Gln His Leu Leu Gln Leu Thr Val Trp Gly Ile Lys Gln
                35                  40                  45

Leu Gln Ala Arg Ile Leu Ala Val Glu Arg Tyr Leu Gly Ser Gly Tyr
            50                  55                  60

Ile Pro Glu Ala Pro Arg Asp Gly Gln Ala Tyr Val Arg Lys Asp Gly
```

Glu Trp Val Leu Leu Ser Thr Phe Leu
            85

<210> SEQ ID NO 13
<211> LENGTH: 57
<212> TYPE: PRT
<213> ORGANISM: Artificial Sequence
<220> FEATURE:
<223> OTHER INFORMATION: N28-Fd2 peptide

<400> SEQUENCE: 13

Ile Glu Ala Gln Gln His Leu Leu Gln Leu Thr Val Trp Gly Ile Lys
1               5                   10                  15

Gln Leu Gln Ala Arg Ile Leu Ala Val Glu Arg Tyr Gly Ser Gly Tyr
            20                  25                  30

Ile Pro Glu Ala Pro Arg Asp Gly Gln Ala Tyr Val Arg Lys Asp Gly
        35                  40                  45

Glu Trp Val Leu Leu Ser Thr Phe Leu
    50                  55

<210> SEQ ID NO 14
<211> LENGTH: 46
<212> TYPE: PRT
<213> ORGANISM: Artificial Sequence
<220> FEATURE:
<223> OTHER INFORMATION: N17-Fd2 peptide

<400> SEQUENCE: 14

Leu Leu Gln Leu Thr Val Trp Gly Ile Lys Gln Leu Gln Ala Arg Ile
1               5                   10                  15

Leu Gly Ser Gly Tyr Ile Pro Glu Ala Pro Arg Asp Gly Gln Ala Tyr
            20                  25                  30

Val Arg Lys Asp Gly Glu Trp Val Leu Leu Ser Thr Phe Leu
        35                  40                  45

<210> SEQ ID NO 15
<211> LENGTH: 41
<212> TYPE: PRT
<213> ORGANISM: Artificial Sequence
<220> FEATURE:
<223> OTHER INFORMATION: C14-Fd1 peptide

<400> SEQUENCE: 15

Trp Met Glu Trp Asp Arg Glu Ile Asn Asn Tyr Thr Ser Leu Gly Tyr
1               5                   10                  15

Ile Pro Glu Ala Pro Arg Asp Gly Gln Ala Tyr Val Arg Lys Asp Gly
            20                  25                  30

Glu Trp Val Leu Leu Ser Thr Phe Leu
        35                  40

<210> SEQ ID NO 16
<211> LENGTH: 48
<212> TYPE: PRT
<213> ORGANISM: Artificial Sequence
<220> FEATURE:
<223> OTHER INFORMATION: C21-Fd1 peptide

<400> SEQUENCE: 16

Trp Met Glu Trp Asp Arg Glu Ile Asn Asn Tyr Thr Ser Leu Ile His
1               5                   10                  15

Ser Leu Ile Glu Glu Gly Tyr Ile Pro Glu Ala Pro Arg Asp Gly Gln

```
                 20                  25                  30

Ala Tyr Val Arg Lys Asp Gly Glu Trp Val Leu Leu Ser Thr Phe Leu
         35                  40                  45

<210> SEQ ID NO 17
<211> LENGTH: 55
<212> TYPE: PRT
<213> ORGANISM: Artificial Sequence
<220> FEATURE:
<223> OTHER INFORMATION: C28-Fd1 peptide

<400> SEQUENCE: 17

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Gly Tyr Ile Pro
            20                  25                  30

Glu Ala Pro Arg Asp Gly Gln Ala Tyr Val Arg Lys Asp Gly Glu Trp
        35                  40                  45

Val Leu Leu Ser Thr Phe Leu
    50                  55

<210> SEQ ID NO 18
<211> LENGTH: 61
<212> TYPE: PRT
<213> ORGANISM: Artificial Sequence
<220> FEATURE:
<223> OTHER INFORMATION: C34-Fd1 peptide

<400> SEQUENCE: 18

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Gly Tyr Ile Pro Glu Ala Pro Arg Asp Gly Gln Ala Tyr Val
        35                  40                  45

Arg Lys Asp Gly Glu Trp Val Leu Leu Ser Thr Phe Leu
    50                  55                  60

<210> SEQ ID NO 19
<211> LENGTH: 63
<212> TYPE: PRT
<213> ORGANISM: Artificial Sequence
<220> FEATURE:
<223> OTHER INFORMATION: C36-Fd1 peptide

<400> SEQUENCE: 19

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu Gly Tyr Ile Pro Glu Ala Pro Arg Asp Gly Gln Ala
        35                  40                  45

Tyr Val Arg Lys Asp Gly Glu Trp Val Leu Leu Ser Thr Phe Leu
    50                  55                  60

<210> SEQ ID NO 20
<211> LENGTH: 65
<212> TYPE: PRT
<213> ORGANISM: Artificial Sequence
<220> FEATURE:
<223> OTHER INFORMATION: C38-Fd1 peptide
```

```
<400> SEQUENCE: 20

Thr Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Gly Tyr Ile Pro Glu Ala Pro Arg Asp Gly
        35                  40                  45

Gln Ala Tyr Val Arg Lys Asp Gly Glu Trp Val Leu Leu Ser Thr Phe
    50                  55                  60

Leu
65

<210> SEQ ID NO 21
<211> LENGTH: 73
<212> TYPE: PRT
<213> ORGANISM: Artificial Sequence
<220> FEATURE:
<223> OTHER INFORMATION: C46-Fd1 peptide

<400> SEQUENCE: 21

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu Asp Lys Trp Ala Ser Leu Trp Asn Trp Phe Gly Tyr
        35                  40                  45

Ile Pro Glu Ala Pro Arg Asp Gly Gln Ala Tyr Val Arg Lys Asp Gly
    50                  55                  60

Glu Trp Val Leu Leu Ser Thr Phe Leu
65                  70

<210> SEQ ID NO 22
<211> LENGTH: 43
<212> TYPE: PRT
<213> ORGANISM: Artificial Sequence
<220> FEATURE:
<223> OTHER INFORMATION: C14-Fd2 peptide

<400> SEQUENCE: 22

Trp Met Glu Trp Asp Arg Glu Ile Asn Asn Tyr Thr Ser Leu Gly Ser
1               5                   10                  15

Gly Tyr Ile Pro Glu Ala Pro Arg Asp Gly Gln Ala Tyr Val Arg Lys
            20                  25                  30

Asp Gly Glu Trp Val Leu Leu Ser Thr Phe Leu
        35                  40

<210> SEQ ID NO 23
<211> LENGTH: 50
<212> TYPE: PRT
<213> ORGANISM: Artificial Sequence
<220> FEATURE:
<223> OTHER INFORMATION: C21-Fd2 peptide

<400> SEQUENCE: 23

Trp Met Glu Trp Asp Arg Glu Ile Asn Asn Tyr Thr Ser Leu Ile His
1               5                   10                  15

Ser Leu Ile Glu Glu Gly Ser Gly Tyr Ile Pro Glu Ala Pro Arg Asp
            20                  25                  30

Gly Gln Ala Tyr Val Arg Lys Asp Gly Glu Trp Val Leu Leu Ser Thr
        35                  40                  45
```

Phe Leu
    50

<210> SEQ ID NO 24
<211> LENGTH: 57
<212> TYPE: PRT
<213> ORGANISM: Artificial Sequence
<220> FEATURE:
<223> OTHER INFORMATION: C28-Fd2 peptide

<400> SEQUENCE: 24

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Gly Ser Gly Tyr
            20                  25                  30

Ile Pro Glu Ala Pro Arg Asp Gly Gln Ala Tyr Val Arg Lys Asp Gly
        35                  40                  45

Glu Trp Val Leu Leu Ser Thr Phe Leu
    50                  55

<210> SEQ ID NO 25
<211> LENGTH: 63
<212> TYPE: PRT
<213> ORGANISM: Artificial Sequence
<220> FEATURE:
<223> OTHER INFORMATION: C34-Fd2 peptide

<400> SEQUENCE: 25

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Gly Ser Gly Tyr Ile Pro Glu Ala Pro Arg Asp Gly Gln Ala
        35                  40                  45

Tyr Val Arg Lys Asp Gly Glu Trp Val Leu Leu Ser Thr Phe Leu
    50                  55                  60

<210> SEQ ID NO 26
<211> LENGTH: 65
<212> TYPE: PRT
<213> ORGANISM: Artificial Sequence
<220> FEATURE:
<223> OTHER INFORMATION: C36-Fd2 peptide

<400> SEQUENCE: 26

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu Gly Ser Gly Tyr Ile Pro Glu Ala Pro Arg Asp Gly
        35                  40                  45

Gln Ala Tyr Val Arg Lys Asp Gly Glu Trp Val Leu Leu Ser Thr Phe
    50                  55                  60

Leu
65

<210> SEQ ID NO 27
<211> LENGTH: 67
<212> TYPE: PRT
<213> ORGANISM: Artificial Sequence
<220> FEATURE:

<223> OTHER INFORMATION: C38-Fd2 peptide

<400> SEQUENCE: 27

Thr Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Gly Ser Gly Tyr Ile Pro Glu Ala Pro Arg
        35                  40                  45

Asp Gly Gln Ala Tyr Val Arg Lys Asp Gly Glu Trp Val Leu Leu Ser
    50                  55                  60

Thr Phe Leu
65

<210> SEQ ID NO 28
<211> LENGTH: 75
<212> TYPE: PRT
<213> ORGANISM: Artificial Sequence
<220> FEATURE:
<223> OTHER INFORMATION: C46-Fd2 peptide

<400> SEQUENCE: 28

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu Asp Lys Trp Ala Ser Leu Trp Asn Trp Phe Gly Ser
        35                  40                  45

Gly Tyr Ile Pro Glu Ala Pro Arg Asp Gly Gln Ala Tyr Val Arg Lys
    50                  55                  60

Asp Gly Glu Trp Val Leu Leu Ser Thr Phe Leu
65                  70                  75

<210> SEQ ID NO 29
<211> LENGTH: 27
<212> TYPE: PRT
<213> ORGANISM: Bacteriophage T4

<400> SEQUENCE: 29

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 30
<211> LENGTH: 29
<212> TYPE: PRT
<213> ORGANISM: Bacteriophage T4

<400> SEQUENCE: 30

Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu
            20                  25

<210> SEQ ID NO 31
<211> LENGTH: 36
<212> TYPE: PRT
<213> ORGANISM: Human immunodeficiency virus

<400> SEQUENCE: 31

```
Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu
        35

<210> SEQ ID NO 32
<211> LENGTH: 28
<212> TYPE: PRT
<213> ORGANISM: Human immunodeficiency virus

<400> SEQUENCE: 32

Ile Glu Ala Gln Gln His Leu Leu Gln Leu Thr Val Trp Gly Ile Lys
1               5                   10                  15

Gln Leu Gln Ala Arg Ile Leu Ala Val Glu Arg Tyr
            20                  25

<210> SEQ ID NO 33
<211> LENGTH: 7
<212> TYPE: PRT
<213> ORGANISM: Human immunodeficiency virus

<400> SEQUENCE: 33

Gln Ile Trp Asn Asn Met Thr
1               5

<210> SEQ ID NO 34
<211> LENGTH: 6
<212> TYPE: PRT
<213> ORGANISM: Human immunodeficiency virus

<400> SEQUENCE: 34

Ile Glu Ala Gln Gln His
1               5

<210> SEQ ID NO 35
<211> LENGTH: 112
<212> TYPE: PRT
<213> ORGANISM: Human immunodeficiency virus

<400> SEQUENCE: 35

Phe Pro Met Gly Ala Ala Ser Met Thr Leu Thr Val Gln Ala Arg Gln
1               5                   10                  15

Leu Leu Ser Gly Ile Val Gln Gln Gln Asn Asn Leu Leu Arg Ala Ile
            20                  25                  30

Glu Ala Gln Gln His Leu Leu Gln Leu Thr Val Trp Gly Ile Lys Gln
            35                  40                  45

Leu Gln Ala Arg Ile Leu Ala Val Glu Arg Tyr Gln Ile Trp Asn Asn
        50                  55                  60

Met Thr Trp Met Glu Trp Asp Arg Glu Ile Asn Asn Tyr Thr Ser Leu
65                  70                  75                  80

Ile His Ser Leu Ile Glu Glu Ser Gln Asn Gln Gln Glu Lys Asn Glu
                85                  90                  95

Gln Glu Leu Leu Glu Leu Asp Lys Trp Ala Ser Leu Trp Asn Trp Phe
            100                 105                 110

<210> SEQ ID NO 36
<211> LENGTH: 34
<212> TYPE: PRT
```

```
<213> ORGANISM: Human immunodeficiency virus

<400> SEQUENCE: 36

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 37
<211> LENGTH: 36
<212> TYPE: PRT
<213> ORGANISM: Human immunodeficiency virus

<400> SEQUENCE: 37

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35
```

STABILIZED TRIMERIC HIV-1 GP41 FUSION INHIBITOR POLYPEPTIDES COMPRISING THE N-TERMINAL HEPTAD REPEAT (NHR) AND FOLDON (FD) TRIMERIZATION MOTIF

CROSS REFERENCE TO RELATED APPLICATIONS

The present application is a division of U.S. patent application Ser. No. 12/702,209 filed Feb. 8, 2010, which claims the benefit under 35 USC §119(e) of U.S. Provisional Patent Application 61/151,110 filed Feb. 9, 2009, the entire contents of both of which are incorporated by reference herein.

STATEMENT REGARDING FEDERALLY SPONSORED RESEARCH OR DEVELOPMENT

This invention was made with United States Government support of Grant No. AI46221 awarded by the National Institutes of Health. The United States Government may have certain rights in this invention.

FIELD OF THE INVENTION

The present disclosure describes trimeric HIV fusion inhibitors comprising peptides corresponding to the sequence of the N-terminal heptad repeat (NHR or HR1) or C-terminal heptad repeat (CHR or HR2) of the transmembrane glycoprotein of HIV and a trimerization motif. Also disclosed are methods of treating HIV infection or preventing HIV sexual transmission by administering such trimeric HIV fusion inhibitors.

BACKGROUND OF THE INVENTION

The human immunodeficiency virus (HIV) is a retrovirus that infects cells of the human immune system, leading to acquired immunodeficiency syndrome (AIDS). In 2007, an estimated 33.2 million people worldwide were living with HIV, about 2.7 million people became newly infected, and 2 million patients lost their lives to AIDS. Currently 25 antiretroviral drugs have been approved by the U.S. Food and Drug Administration (FDA) for treating HIV infection, 22 of which are reverse transcriptase inhibitors (RTIs) and protease inhibitors (PIs). RTIs inhibit the activity of HIV reverse transcriptase, a viral DNA polymerase enzyme that HIV needs to reproduce, while PIs inhibit the activity of HIV protease, an enzyme used by the virus to cleave nascent proteins for the final assembly of new virions. Clinical applications of these drugs in different combinations, known as highly active antiretroviral therapy (HAART), have dramatically reduced the morbidity and mortality of AIDS and have significantly improved life expectancy for HIV-infected patients. However, increasing numbers of HIV/AIDS patients on HAART regimens have failed to respond to the current RTIs and PIs due to the emergence of variant strains of drug-resistant HIV. Thus, there is an urgent need for development of new antiretrovirals which are active in inhibiting HIV fusion and entry and against HIV strains that are resistant to current HAART regimens.

Sexual transmission is the most common route of spread of HIV. Both cell-free and cell-associated HIV present in the genital secretions can be sexually transmitted. The continual spread of the HIV epidemic is testament to the lack of safe sex practices. Thus there is an urgent need to develop topically applicable, safe, potent and affordable anti-HIV agent for prevention of HIV sexual transmission.

The event of viral fusion and entry mediated by viral envelope glycoproteins (Env) gp120 and gp41 is the first and most essential step of HIV type 1 (HIV-1) infection. After gp120 binding to the cellular receptor CD4 and a coreceptor, CXCR4 or CCR5, the fusion peptide at the N-terminus of gp41 is exposed, enabling its insertion into the target cell membrane. A series of conformational changes in gp41 take place which lead the protein into its fusogenic state, bringing the viral and target cell membranes into close proximity and promoting membrane fusion.

The core structure of the gp41 ectodomain consists of two 4-3 hydrophobic heptad repeat (HR) regions defined as N-terminal heptad repeat (NHR or HR1, residues 540-590) and C-terminal heptad repeat (CHR or HR2, residues 624-666). Crystallographic studies have shown that CHR can interact with NHR to form a conformation called the "trimer-of-hairpins" or "six-helix bundle" (6-HB), within which three parallel NHRs form a trimeric coiled-coil core and three CHRs pack antiparallelly into the highly conserved hydrophobic grooves along the surface of the inner coiled coil.

Peptides derived from NHR and CHR regions are named NHR- and CHR-peptides, respectively. Some CHR-peptides are potent HIV fusion inhibitors, acting by binding to the viral gp41 inner NHR-trimer to interfere with 6-HB formation. In the early 1990s, the first highly potent CHR-peptide with anti-HIV activity at nanomolar level, SJ-2176, was discovered. Later, two analog peptides, T20 (DP-178) and C34, which inhibited HIV-1-mediated fusion at low nanomolar level were reported. T20 (Fuzeon®; enfuvirtide) has been approved by the US FDA as the first member of a new class of anti-HIV drugs—HIV fusion inhibitors.

T20 is effective as a salvage therapy for HIV/AIDS patients who have failed to respond to current antiretroviral therapeutics, including RTIs and PIs. However, the clinical use of T20 is limited because of its low potency, short half-life, high cost of production and ease with which it induces drug resistance. Using molecular cloning techniques to express recombinant proteins comprising the CHR-sequence fused to a trimerization motif is expected to produce a CHR-trimer with improved potency, relatively long half-life, lower cost of production, and improved resistance profile.

Besides CHR, NHR is also a key target of engineered peptide or protein inhibitors. An NHR-targeted molecule, designed 5-Helix, consists of three NHR helices and two CHR helices interconnected by linkers of five amino acids each. This peptide folds into a structure similar to 6-HB, in which a hydrophobic groove between two NHR-helices is exposed for the binding of viral CHR. 5-Helix shows high potency against HIV-1 infection with a low nanomolar $IC_{50}$ value. However, it is a difficult task to refold the polypeptide into 5-helix bundle.

In principle, NHR-peptides should also present antiviral activity by targeting the CHR to block the binding of viral CHR to NHR. But the potency of linear NHR-peptides is very low. The reason is that NHR-peptides tend to aggregate in the absence of CHR-peptides. It is supposed that if properly designed NHR-peptides could form stable trimeric coiled-coil conformations that do not aggregate, their efficiency should be as high as that of CHR-peptides.

There are several ways to construct soluble NHR-trimers. Firstly, intermolecular disulfide bonds can be introduced in the NHR-peptide region to stabilize the trimeric conformation. Examples of this method include N34CCG and N35CCG-N13. Secondly, NHR-peptides can be fused to the designed trimetic coiled coils such as portions of GCN4-pIQI (IQ) or IZ to form stable helical trimers, e.g., IQN17, IQN23, and IZN17. These soluble NHR-trimers may inhibit HIV infection as effective as the CHR-peptides.

In the present disclosure, an NHR- or CHR-peptide was linked to a peptide corresponding to the sequence of foldon (Fd), a trimerization motif in the C-terminal domain of T4 fibritin, to form a highly stable and soluble NHR-trimer or CHR-trimer, which are expected to be more potent against HIV infection, more soluble and stable than the monomeric NHR- or CHR-peptides, respectively.

BRIEF DESCRIPTION OF THE DRAWINGS

FIG. 2 depicts the interactions between the NHR and CHR of gp41 and between N- and C-peptides. The dashed lines between NHR and CHR indicate the interaction between the residues located at the e and g positions in the NHR and the a and d positions in the CHR. N36 (SEQ ID NO:30); N28 (SEQ ID NO:31); C34 (SEQ ID NO:35); T20 (SEQ ID NO:36); gp41 (SEQ ID NO:37).

FIG. 3 depicts the sequences of N36Fd and N28Fd. The NHR and CHR sequences are underlined and double underlined, respectively. The pocket-forming sequence (aa 565-581) in the NHR and pocket-binding domain (aa 628-635) in the CHR are in bold and italic type, respectively. The Fd sequence is bolded and underlined. N36Fd (SEQ ID NO:1); N28Fd (SEQ ID NO:6).

SUMMARY OF THE INVENTION

Figure 1:
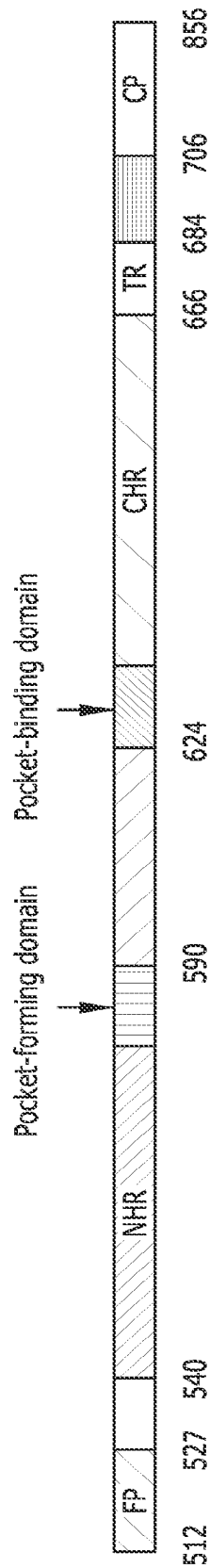
FIG. 1 depicts the schematic view of gp41 functional domains. The residue number corresponds to its position in HIV-1$_{HXB2}$ gp160. FP, fusion peptide; TR, tryptophan-rich region; TM, transmembrane domain; CP, cytoplasmic domain.

In one aspect, disclosed herein are trimeric HIV fusion inhibitors consisting of a peptide corresponding to the sequence of the N-terminal heptad repeat (NHR or HR1) or C-terminal heptad repeat (CHR or HR2) of the transmembrane glycoprotein of HIV and a peptide corresponding to foldon (Fd) for the treatment of HIV infections.

In another aspect, disclosed herein is the use of trimeric HIV fusion inhibitors consisting of peptides corresponding to the sequence of the NHR (or HR1) or CHR (or HR2) of the transmembrane glycoprotein of HIV and a peptide corresponding to Fd for the prevention of HIV sexual transmission.

In another aspect, disclosed herein is the use of NHR-trimer HIV fusion inhibitors, including the amino acid sequence of SEQ ID NOs. 1-14, for the treatment of HIV infections or prevention of HIV sexual transmission.

In another aspect, disclosed herein is the use of CHR-trimer HIV fusion inhibitors, including the amino acid sequence of SEQ ID NOs. 15-28, for the treatment of HIV infections or prevention of HIV sexual transmission.

In additional aspect, disclosed herein is the use of conservatively modified variants of SEQ ID NOs. 1-28 for treatment of HIV infections or prevention of HIV sexual transmission.

In additional aspect, disclosed herein is the use of NHR- or CHR-trimer HIV fusion inhibitors in combination with other anti-HIV drugs for treatment of HIV infections or prevention of HIV sexual transmission.

In additional aspect, the NHR- or CHR-trimer HIV fusion inhibitors are administered in a manner selected from the group consisting of intramuscular, intravenous, subcutaneous, oral, mucosal, vaginal, rectal and percutaneous administration.

Disclosed herein are trimeric polypeptide pharmaceutical compositions comprising three monomers, each monomer comprising a peptide having the amino acid sequence of the N-terminal heptad repeat (NHR or HR1) or C-terminal heptad (CHR or HR2) of the transmembrane glycoprotein of human immunodeficiency virus (HIV) and a trimerization motif. In another embodiment, the trimeric polypeptide pharmaceutical composition is produced by recombinant DNA technology.

In another embodiment, the trimerization motif is foldon. In another embodiment, the polypeptide comprises a N-terminal heptad repeat and said polypeptide comprises the amino acid sequence of one of SEQ ID NOs. 1-14. In yet another embodiment, the polypeptide comprises the amino acid sequence of SEQ ID NO. 1.

In another embodiment, the polypeptide comprises a C-terminal heptad repeat and said polypeptide comprises the amino acid sequence of one of SEQ ID NOs. 15-28. In another embodiment, the polypeptide comprises the amino acid sequence of SEQ ID NO. 15.

In another embodiment, the trimeric polypeptides are homotrimers.

In one embodiment, a method is provided of inhibiting the fusion of a human immunodeficiency virus to a target cell comprising administering a trimeric polypeptide pharmaceutical composition and inhibiting fusion of the virus to the cell. In another embodiment, the method prevents infection of a subject with human immunodeficiency virus. In yet another embodiment, the method treats a patient previously infected with human immunodeficiency virus.

DETAILED DESCRIPTION OF THE INVENTION

In one embodiment, disclosed herein is the use of NHR- or CHR-trimer HIV fusion inhibitors for treatment of HIV infection or prevention of HIV sexual transmission.

The term "HIV fusion" refers to a critical step of virus life cycle necessary for a virion or HIV-infected cell fusing with a target vesicle or cell.

The term "HIV fusion inhibitor" refers to any agent that blocks HIV or HIV-infected cell fusion with a target vesicle or cell.

The term "NHR-trimer" refers to a trimer formed by peptides derived from the NHR (or HR1) sequence of the transmembrane glycoprotein of HIV. The term "NHR monomer" refers to a peptide comprising an NHR peptide sequence and a trimerization motif. For purposes of the present disclosure, the terms "peptide" and "polypeptide" are used interchangeably.

The term "CHR-trimer" refers to a trimer formed by peptides derived from the CHR (or HR2) sequence of the transmembrane glycoprotein of HIV. The term "CHR monomer" refers to a peptide comprising a CHR peptide sequence and a trimerization motif.

The present inventors designed a soluble trimer of NHR, or CHR, peptides stabilized with a trimerization motif, foldon (Fd), a 27 amino acid region of the C-terminal domain of T4 fibritin (GYIPEAPRDGQAYVRKDGEWVLLSTFL, SEQ ID NO: 29 or GSGYIPEAPRDGQAYVRKDGEWVLLSTFL, SEQ ID NO:30). Foldon is obligatory for the formation of the fibritin trimer structure and can be used as an artificial trimerization domain. Its native structure consists of a trimeric β-hairpin propeller. Chimeric proteins can be produced, comprising the foldon domain connected at the C-terminal end of selected NHR, or CHR, sequences with or without the use of a natural linker sequence, which results in the folding of the resultant fusion protin into highly stable, SDS-resistant trimers.

In one embodiment, the NHR peptide is selected from the group consisting of N36, N46, N56, N54, N60, N28, N17 and N51. In another embodiment, the CHR peptide is selected from the group consisting of C14, C21, C28, C34, C36, C38 and C46. The amino acid sequences of NHR and CHR peptides and NHR and CHR monomers are presented in Table 2.

In one embodiment, the NHR monomer comprises the amino acid sequence of SGIVQQQNNLL-RAIEAQQHLLQLTVWGIKQLQARILGYI-PEAPRDGQAYVRKDGEW VLLSTFL (SEQ ID NO. 1).

As used herein, the single-letter codes represent amino acid residues: A, Alanine; R, Arginine; N, Asparagine; D, Aspartic acid; C, Cysteine; Q, Glutamine; E, Glutamic acid; G, glycine; H, Histidine; I, Isoleucine; L, Leucine; K, Lysine; M, Methionine; F, Phenylalanine; P, Proline; S, Serine; T, Threonine; W, Tryptophan; Y, Tyrosine; V, Valine.

In another embodiment, the NHR monomer comprises the amino acid sequence of one of SEQ ID NOs. 2-14.

In another embodiment, the CHR monomer comprises the amino acid sequence of WMEWDREINNYTSLGYI-PEAPRDGQAYVRKDGEWVLLSTFL (SEQ ID NO. 15).

In another embodiment, the CHR monomer comprises the amino acid sequence of one of SEQ ID NOs. 16-28.

In additional embodiments, disclosed herein is the use of conservatively modified variants of SEQ ID NOs. 1-28 for treatment of HIV infections or prevention of HIV sexual transmission. The variants described herein maintain the biological activity of the parent or source molecule.

As used herein the term "conservatively modified variants" refers to variant peptides which have the same or similar biological activity of the original peptides. For example, conservative amino acid changes may be made, which although they alter the primary sequence of the protein or peptide, do not alter its function. Conservative amino acid substitutions typically include substitutions within the following groups: glycine and alanine; valine, isoleucine, and leucine; aspartic acid and glutamic acid; asparagine and glutamine; serine and threonine; lysine and arginine; phenylalanine and tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g. by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides disclosed herein are not limited to products of any of the specific exemplary processes listed herein.

In addition to substantially full length polypeptides, the present disclosure also provides for biologically active fragments of the polypeptides.

As used herein, amino acid sequences which are substantially the same typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present disclosure. As readily recognized by those of skill in the art, various ways have been devised to align sequences for comparison, e.g., Blosum 62 scoring matrix, as described by Henikoff and Henikoff in Proc. Natl. Acad Sci. USA 89:10915 (1992). Algorithms conveniently employed for this purpose are widely available (see, for example, Needleman and Wunsch in J. Mol. Bio. 48:443 (1970).

Therefore, disclosed herein are amino acid sequences 85%, 90%, 95%, 98%, 99% or 100% identical to SEQ ID NOs:1-32.

Upon expression from the appropriate expression system, the NHR or CHR peptides spontaneously form trimers. In another embodiment, heterologous trimers are disclosed in which two or three different monomers form the trimer. To form a trimer with different monomeric peptides, the trimers of different N-peptide-Fd (e.g., N28Fd and N36Fd) are broken apart with a denaturing agent (e.g., 6M GuHCl). After mixing the dissociated monomers together, and removing the denaturing agent, the different monomers form heterologous trimers.

The following expression systems are suitable for use in expressing the disclosed trimeric proteins: mammalian cell expression systems such as, but not limited to, pcDNA expression system, and GS Gene expression system; insect cell expression systems such as, but not limited to, Bac-to-Bac expression system, baculovirus expression system and DES expression systems; and E. coli expression systems including, but not limited to, pET, pSUMO and GST expression systems.

The term "therapeutic effect" refers to one or more of the following: 1) inhibition of fusion of a virion or HIV-infected cell with a target cell; 2) inhibition of HIV replication; 3) reduction in the number of infected cells; 4) reduction in the concentration of virions present in serum; 5) increasing T-cell count; 6) relieving or reducing to some extent one or more of the symptoms associated with HIV; and 7) relieving or reducing the side effects associated with the administration of other antiretroviral agents.

"Therapeutically effective amount" is intended to qualify the amount required to achieve a therapeutic effect.

"$EC_{50}$ and $EC_{90}$" refer to the drug concentration that results in a 50% and 90% reduction, respectively, in virus replication or virus-mediated cell-cell fusion.

The present disclosure is also directed to pharmaceutical compositions comprising the above-described trimeric peptides. Dosages and desired drug concentrations of the disclosed trimeric pharmaceutical compositions may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mardenti, J. and Chappell, W. "The use of interspecies scaling in toxicokinetics" In Toxicokinetics and New Drug Development, Yacobi et al, Eds., Pergamon Press, New York 1989, pp. 42-96. "Treatment" refers to both therapeutic treatment and prophylactic or preventative measures, wherein the object is to prevent or slow down (lessen) the targeted pathologic condition or disease. Those in need of treatment include those already with the disease as well as those prone to have the disease or those in whom the disease is to be prevented. In one embodiment, the disease is present. In another embodiment, the life of a cell or an individual is prolonged due to the methods described herein.

The above-described trimeric peptides can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, nasal, lingual, sublingual, buccal, intrabuccal, intravenous, subcutaneous, intramuscular and pulmonary administration can be made without undue experimentation by means well known in the art, for example with an inert diluent or with an pharmaceutically acceptable carrier. The compositions are enclosed in gelatin capsules or compressed into tablets. For the purpose of oral therapeutic administration, the pharmaceutical compositions may be incorporated with excipients and used in the form of tablets, troches, capsules, elixirs, suspensions, syrups, wafers, chewing gums and the like. A "pharmaceutically acceptable carrier" means any of the standard pharmaceutical carriers. Examples of suitable carriers are well known in the art and may include but are not limited to any of the standard pharmaceutical carriers like phosphate buffered saline solutions, phosphate buffered saline containing polysorbate 80, water, emulsions such as oil/water emulsion, and various types of wetting agents. Other carriers may also include sterile solutions, tablets, coated tablets, and capsules. Typically such carriers contain excipients like starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

Tablets, pills, capsules, troches and the like may also contain binders, excipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The trimeric compositions can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the trimeric compositions, in a pharmaceutical composition, into the rectum or large intestine. This can be accomplished using suppositories, enemas, gels, creams, tablets, and the like. Suppository formulations can easily be made by methods known in the art. Similarly, vaginal administration forms comprising suppositories, gels, douches, creams, tablet, rings and the like can be formulated. The composition may be intended for rectal or vaginal administration, in the form, e.g., of a suppository which will melt in the rectum and release the drug. The composition for rectal or vaginal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the cyclohexylamine compound is dispersed homogeneously therein by stirring. The molten homogeneous mixture is then poured into convenient sized molds, allowed to cool and thereby solidify.

The disclosed compositions intended for topical administration may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration.

Transdermal administration includes percutaneous absorption of the composition through the skin. Transdermal formulations include patches, iontophoresis devices, ointments, creams, gels, salves and the like.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The trimeric peptide compositions of the present disclosure may be administered in a therapeutically effective amount, according to an appropriate dosing regiment. As understood by a skilled artisan, the exact amount required may vary from subject to subject, depending on the subject's species, age and general condition, the severity of the infection, the particular agent(s) and the mode of administration. In some embodiments, about 0.001 mg/kg to about 50 mg/kg, of the composition based on the subject's body weight is administered, one or more times a day, to obtain the desired therapeutic effect. In other embodiments, about 1 mg/kg to about 25 mg/kg, of the composition based on the subject's body weight is administered, one or more times a day, to obtain the desired therapeutic effect.

The total daily dosage of the compositions will be determined by the attending physician within the scope of sound medical judgment. The specific therapeutically effective dose level for any particular patient or subject will depend upon a variety of factors including the disorder being treated and the severity of the disorder; the activity of the specific compound employed; the specific composition employed; the age, body weight, general health, sex and diet of the patient or subject; the time of administration, route of administration, and rate of excretion of the specific compound employed; the duration of the treatment; drugs used in combination or coincidental with the specific compound employed, and other factors well known in the medical arts.

The disclosed compositions may also be employed in combination therapies. That is, the compositions presently disclosed can be administered concurrently with, prior to, or subsequent to, one or more other desired compositions, therapeutics, treatments or medical procedures. The particular combination of therapies administered will be determined by the attending physician and will take into account compatibility of the treatments and the desired therapeutic effect to be achieved. It will be appreciated that therapeutically active agents utilized in combination may be administered together in a single composition, treatment or procedure, or alternatively may be administered separately.

For example, the disclosed compositions may be administered in combination with one or more other HIV inhibitors including, for example, but not limited to, one or more nucleoside/nucleotide reverse transcriptase inhibitors (NRTIs), non-nucleoside reverse transcriptase inhibitors (NNRTIs), protease inhibitors (PIs), fusion inhibitors, integrase inhibitors, chemokine receptor (CXCR4, CCR5) inhibitors and/or hydroxyurea.

Nucleoside reverse transcriptase inhibitors, include but are not limited to, abacavir (ABC; ZIAGEN®), didanosine (dideoxyinosine (ddI); VIDEX®), lamivudine (3TC; EPIVIR®), stavudine (d4T; ZERIT®, ZERIT XR®), zalcitabine (dideoxycytidine (ddC); HIVID®), zidovudine (ZDV, formerly known as azidothymidine (AZT); RETROVIR®), abacavir, zidovudine, and lamivudine (TRIZIVIR®), zidovudine and lamivudine (COMBIVIR®), and emtricitabine (EMTRIVA®). Nucleotide reverse transcriptase inhibitors include tenofovir disoproxil fumarate (VIREAD®). Non-nucleoside reverse transcriptase inhibitors for HIV include, but are not limited to, nevirapine (VIRAMUNE®), delavirdine mesylate (RESCRIPTOR®), and efavirenz (SUSTIVA®).

Protease inhibitors (PIs) include amprenavir (AGENERASE®), saquinavir mesylate (FORTOVASE®, INVIRASE®), ritonavir (NORVIR®), indinavir sulfate (CRIXIVAN®), nelfmavir mesylate (VIRACEPT®), lopinavir and ritonavir (KALETRA®), atazanavir (REYATAZ®), and fosamprenavir (LEXIVA®). Atazanavir and fosamprenavir (LEXIVA®) are new protease inhibitors that were recently approved by the U.S. Food and Drug Administration for treating HIV-1 infection (see atazanavir (REYATAZ®) and emtricitabine (EMTRIVA®) for HIV infection, Medical Letter on Drugs and Therapeutics, available online at www.medletter.com; U.S. Department of Health and Human Services (2003). Guidelines for the Use of Antiretroviral Agents in HIV-infected Adults and Adolescents; available online at aidsinfo.nih.gov/guidelines.

A fusion/entry inhibitor attaches to the outside of a CD4+ cell (a type of white blood cell) or coreceptors such as CCR5 and CXCR4 or to the viral membrane proteins, such as gp41 and gp120. Fusion/entry inhibitors prevent fusion between the virus and the cell from occurring or entry of the virus to the cells and therefore, prevent HIV infection and multiplication. Fusion/entry inhibitors include, but are not limited to, enfuvirtide (FUZEON®) and maraviroc (SELZENTRY®, Pfizer).

An integrase inhibitor blocks the action of integrase, preventing HIV-1 genetic material from integrating into the host DNA, and thereby stopping viral replication. Integrase inhibitors include, but are not limited to, raltegravir (ISENTRESS®, Merck); and elvitegravir (GS 9137, Gilead Sciences).

Alternatively or additionally, the compositions disclosed herein may be administered in combination with one or more anti-infective agents (e.g., antibiotics, etc.), pain relievers, or other agents intended to address symptoms of one or more diseases, disorders, or conditions commonly found in immunocompromised individuals but not directly caused by HIV.

EXAMPLE 1

Design of N36Fd and N28Fd Trimers

N-peptides derived from the HIV-1 gp41 NHR are commonly regarded as weak HIV-1 fusion inhibitors because free N-peptides have a tendency to aggregate and thus cannot fold into a stable trimeric α-helical conformation in physiological solution. The 27-mer Fd sequence (SEQ ID NO: 29) was used to facilitate the trimerization of the N-peptides N36 and N28 by fusing the Fd sequence directly to the C-terminus of N36 (SEQ ID NO: 30) or N28 (SEQ ID NO: 31) without any linking sequence (FIG. 3). N36 was chosen for this study because of its ability to form highly stable 6-HB with peptides derived from gp41 CHR. This peptide includes a 17-amino acid sequence that provides a critical hydrophobic pocket for the interaction between gp41 NHR and CHR (FIG. 2, in bold). The N28 peptide was selected because of an AVERY (aa 582-586) sequence adjacent to the C-terminus of the pocket-formation sequence which may be important for gp41 6-HB formation. Specifically, the C-peptides CP-32 (aa 621-652) and CP-32M, which contain an AVERY-binding motif, QIWNNMT (aa 621-627; SEQ ID NO:33) (FIG. 2), are more potent than T20 in blocking 6-HB formation and inhibiting infection by HIV-1 strains, including those resistant to T20 and C34. N28 contains the 17-mer pocket-forming sequence (N17) plus the 6-mer IEAQQH (aa 559-564; SEQ ID NO:34)) sequence and the 5-mer AVERY motif at the N- and C-termini of N17 sequence, respectively (FIG. 2). Addition of the short flanking sequences at both sides of the pocket-forming sequence may improve refolding and solubility of the highly hydrophobic pocket sequence in N28. The full length of the designed N36Fd and N28Fd peptides consists of 63 and 55 amino acid residues (FIG. 3), respectively. Peptides longer than 50 amino acids are technically difficult to synthesize, but can be well expressed in *E. coli*.

EXAMPLE 2

Expression, Purification and Characterization of N36Fd and N28Fd

The DNA fragments of N36 and N28 were amplified by PCR using the Platinum PCR SuperMix High Fidelity kit (Invitrogen, Carlsbad, Calif.) from a pHBX-env/wt plasmid with a forward primer containing a BamH1 site and a reverse primer that had no restriction site. The fragment of Fd was produced by annealing a long synthetic forward primer coding the last 9 amino acids of the N-peptide (N36 or N28) and the Fd with its complement, a long reverse primer with an Xho1l site. Then the two overlapping fragments were mixed and used as templates for another PCR reaction using the BamH1 forward primer and a shorter reverse primer coding the last few amino acids of the Fd with an Xho1l site. The product was purified using a gel extraction kit (QIAGEN, Valencia, Calif.), digested with BamH1 and Xho1l enzymes (TaKaRa Bio, Madison, Wis.), and cloned into a pGEX6p-1 vector (QIAGEN). The sequence was confirmed by DNA sequencing.

Either the N36Fd-pGEX6p-1 or N28Fd-pGEX6p-1 plasmid was transformed into *Escherichia coli* Rosetta 2(DE3) (Novagen, Gibbstown, N.J.). The cells were incubated at 37° C. in LB medium until the $OD_{600}$ reached 0.8-1.0. The culture was induced with 0.4 mM IPTG and incubated at 30° C. for 4 h. Then, the cells were harvested and broken by sonication in 1% Triton PBS buffer. After the samples were centrifuged, the supernatant was loaded into a GST-bind column (Novagen). The column was rinsed, and the bound GST-fused N-Fd peptides were then cleaved on the column with PreScission Protease (GE Healthcare UK Ltd., Buckinghamshire, UK) in cleavage buffer (50 mM Tris-HCl pH7.0, 150 mM NaCl, 1 mM EDTA, 1 mM dithiothreitol) at 4° C. overnight. The cleaved peptides were eluted from the column on the next day by washing with cleavage buffer. Either the N36Fd or N28Fd in this rough product was further separated from GST by a series of ultrafiltrations using Amicon Ultra-15 Centrifugal Filter Devices (Millipore, Billerica, USA). N36Fd and N28Fd performed monomeric conformation in the buffer with pH lower than 3.0, which enabled them to be collected in the centrifuge tube of the 30KD Ultra-15 Centrifugal Filter Device, while GST was kept in the filter unit. Finally, the N-Fd peptide was dialyzed against $ddH_2O$ (pH 7.0) and refolded into trimers using the 10KD Ultra-15 Centrifugal Filter Device.

Figure 4:
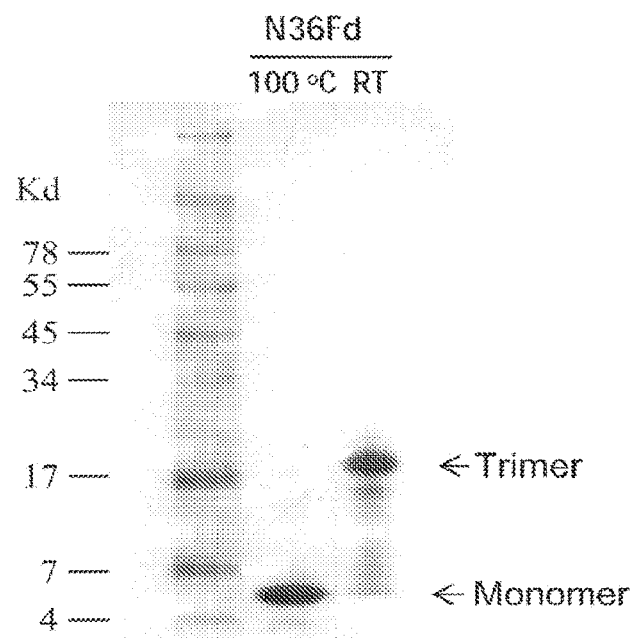
FIG. 4 depicts SDS-PAGE gel electrophoresis showing that N36Fd is a SDS-resistant but heat-sensitive trimer.
Figure 5:
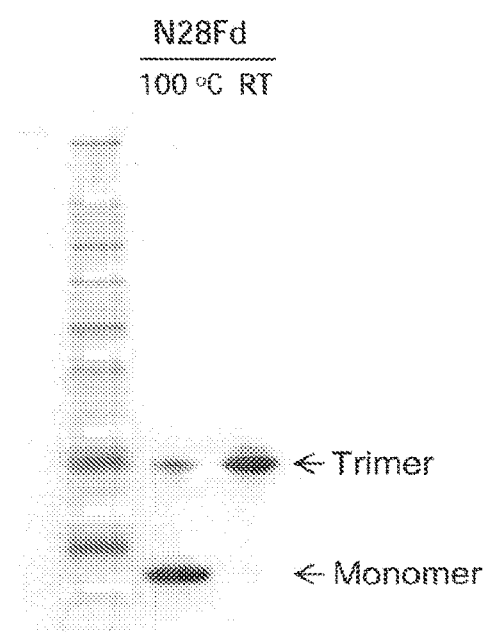
FIG. 5 depicts SDS-PAGE gel electrophoresis showing that N28Fd is a SDS-resistant but heat-sensitive trimer.

Purified N36Fd and N28Fd were analyzed by SDS-PAGE. Briefly, 5 μl/well of 100 μM N36Fd or N28Fd was mixed with 4×SDS sample buffer (Novagen). The sample was boiled for 5 min or kept at room temperature (RT) before loading onto a 10-20% Tricine-Glycine gel (Invitrogen). The electrophoresis was conducted in SDS-PAGE running buffer with 125V constant voltage at 4° C. The gels were stained with SimplyBlue SafeStain (Invitrogen). After boiling for 5 min in the presence of 2% SDS, N36Fd was denatured and exhibited a band in the gel corresponding to the monomer form. N36Fd treated with SDS buffer under room temperature exhibited one major band corresponding to the trimeric form and a number of minor bands with lower molecular size (FIG. 4). This result suggests that a major portion of the N36Fd maintains trimeric conformation in SDS buffer at RT. A major monomer band and a minor trimer band were revealed when N28Fd was treated by boiling for 5 min, while only one band corresponding to the trimeric form was shown when N28Fd was treated in SDS buffer at RT (FIG. 5). These results suggest that N28Fd, as a trimer, is more stable than N36Fd under SDS conditions.

EXAMPLE 3

N36Fd and N28Fd are in a Stable Alpha-Helical Conformation

The secondary conformational structure of N36, N36Fd, N28, N28Fd and Fd peptides was analyzed by circular dichroism (CD) spectroscopy as previously described. All the N-peptides were diluted in $ddH_2O$ (pH 7.0) and all the C-peptides or the mixture of the N- and C-peptides were diluted in 50 mM sodium phosphate and 150 mM NaCl (PBS, pH 7.2) to a final concentration of 10 μM. The individual peptides and their mixtures were incubated in a 37° C. water bath for 0.5 h before testing. The spectra of each sample were acquired on Jasco spectropolarimeter (Model J-715, Jasco Inc., Japan) at RT, using a 5.0 nm bandwidth, 0.1 nm resolution, 0.1 cm path length, 4.0 sec response time, and a 50 nm/min scanning speed, and were corrected by a subtraction of the background corresponding to the solvent. The spectrum of the N-peptide portion in the individual N36Fd or N28Fd, or in the N36Fd/C34 or N28Fd/C34 mixture, was calculated by subtracting the spectrum of free Fd peptide from that of N36Fd, N28Fd, N36Fd+C34 or N28Fd+C34. The α-helicity was calculated from the CD signal by dividing the mean residue ellipticity at 222 nm by the value expected for 100% helix formation (i.e., 33,000° $cm^2$ $dmol^{-1}$) according to previous studies. Thermal denaturation of the samples was monitored at 222 nm by applying a temperature gradient from 20° C. to 98° C. with a 2-degree interval, an equilibration time of 1.5 min, and an averaging time of 60 s. The midpoint of the thermal unfolding transition (Tm) values was calculated using Jasco software utilities as described previously.

Figure 6:
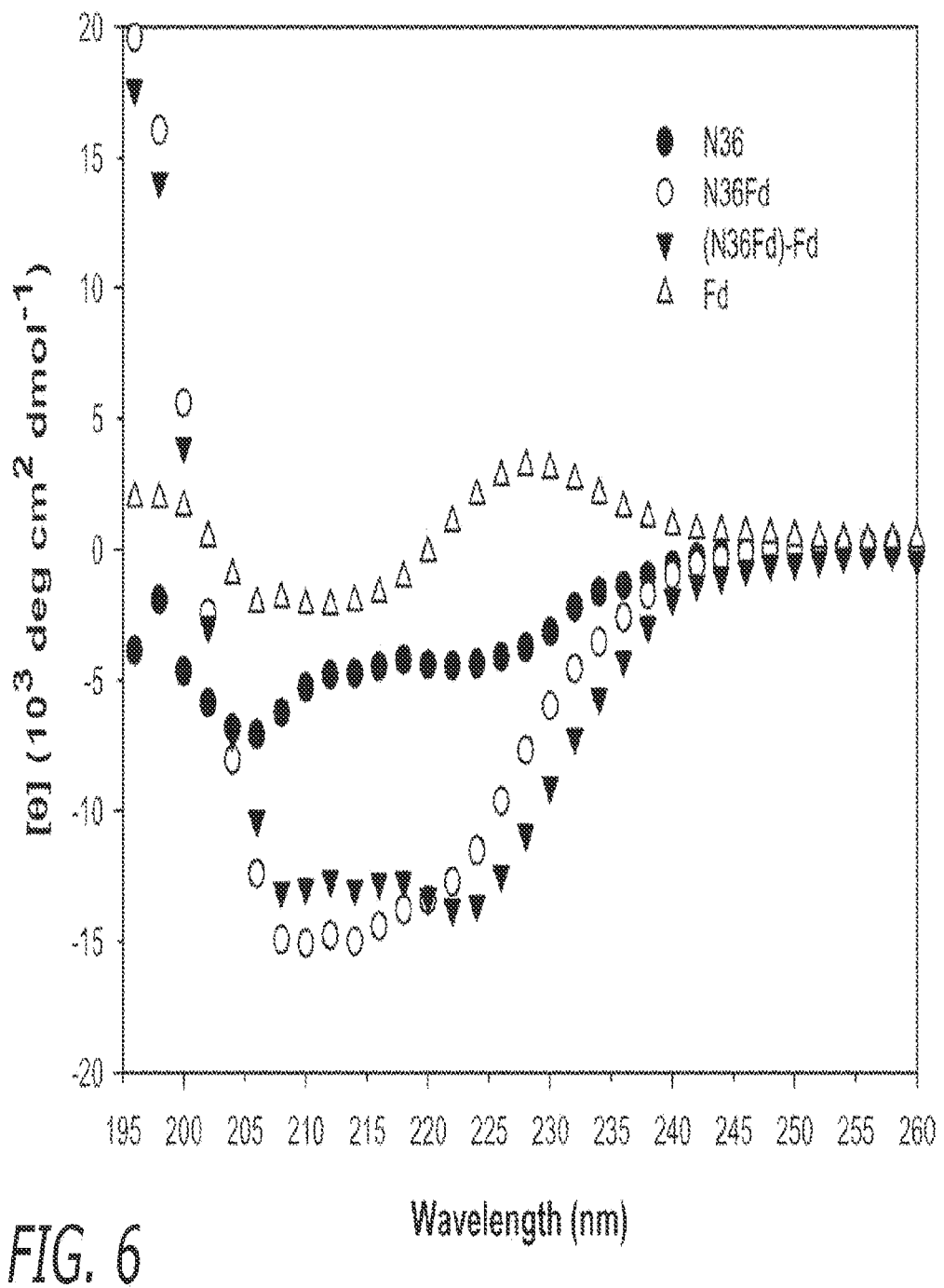
FIG. 6 illustrates CD spectroscopy analysis of the secondary structures of N36 and N36Fd. The spectra of (N36Fd)-Fd was calculated by subtracting the spectra of Fd peptide from those of N36Fd.
Figure 7:
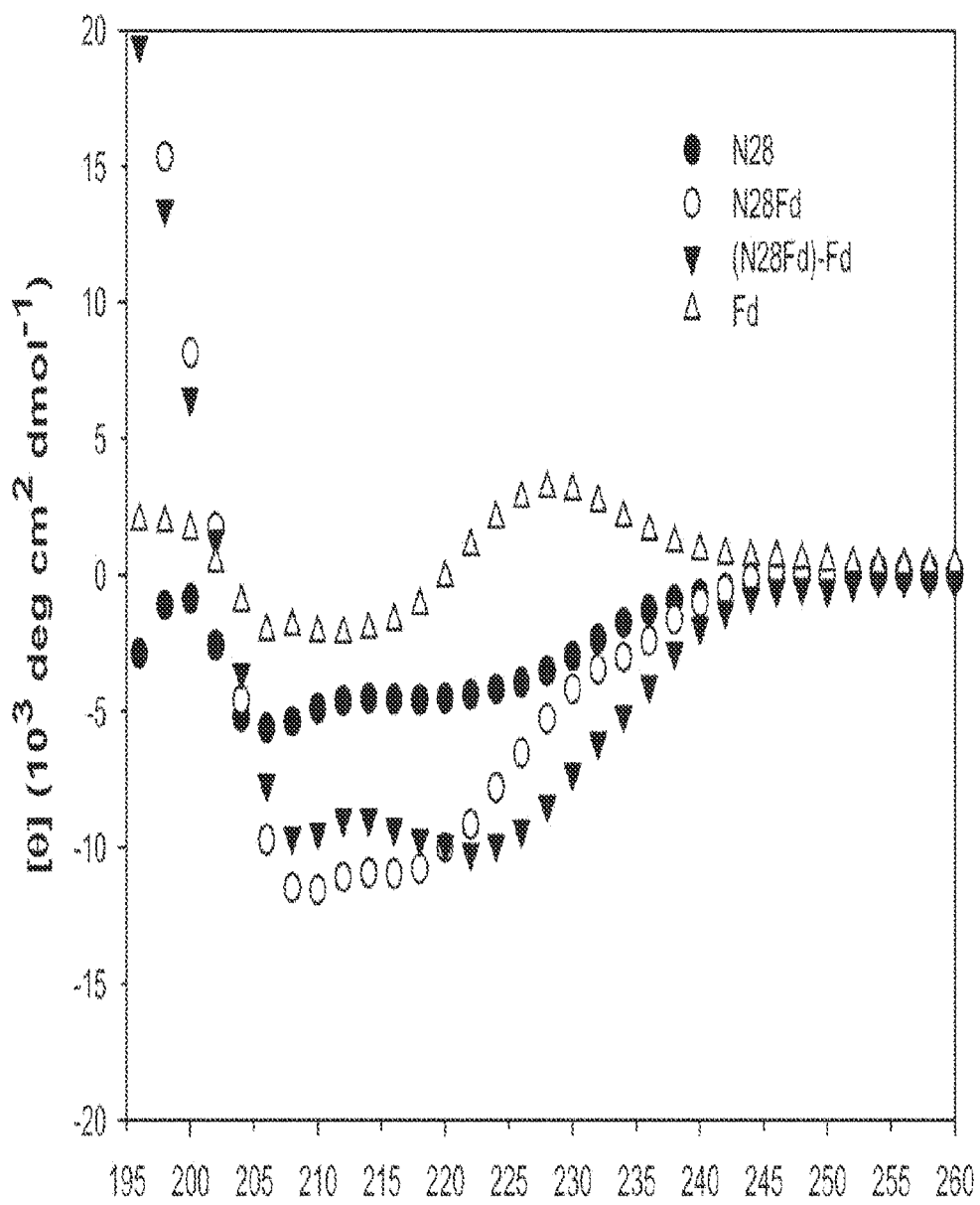
FIG. 7 illustrates CD spectroscopy analysis of the secondary structures of N28 and N28Fd. The spectra of (N28Fd)-Fd was calculated by subtracting the spectra of Fd peptide from those of N28Fd.

Free Fd peptide and N-peptides presented little α-helicity. Unexpectedly, the chimeric N36Fd and N28Fd did not exhibit typical α-helical spectra either, but rather a mixture of α-helix and β-sheet conformation (FIGS. 6 and 7). Indeed, after subtraction of the spectra of free Fd peptide, which consists of β-sheet structure, from those of N36Fd or N28Fd, a typical α-helical spectrum was revealed (FIGS. 6 and 7). These results indicate that the Fd domain in the N36Fd and N28Fd greatly facilitated N-peptide folding into trimeric α-helical conformation, mimicking the conformation of NHR-trimer in the fusion intermediate state of the HIV-1 gp41. The α-helicity of the N36 or N28 portion in N36Fd or N28Fd was 41.7% and 30.9%, respectively.

EXAMPLE 4

N36Fd and N28Fd Form Highly Stable Six-Helix Bundle with CHR-Peptide C34

Figure 8:
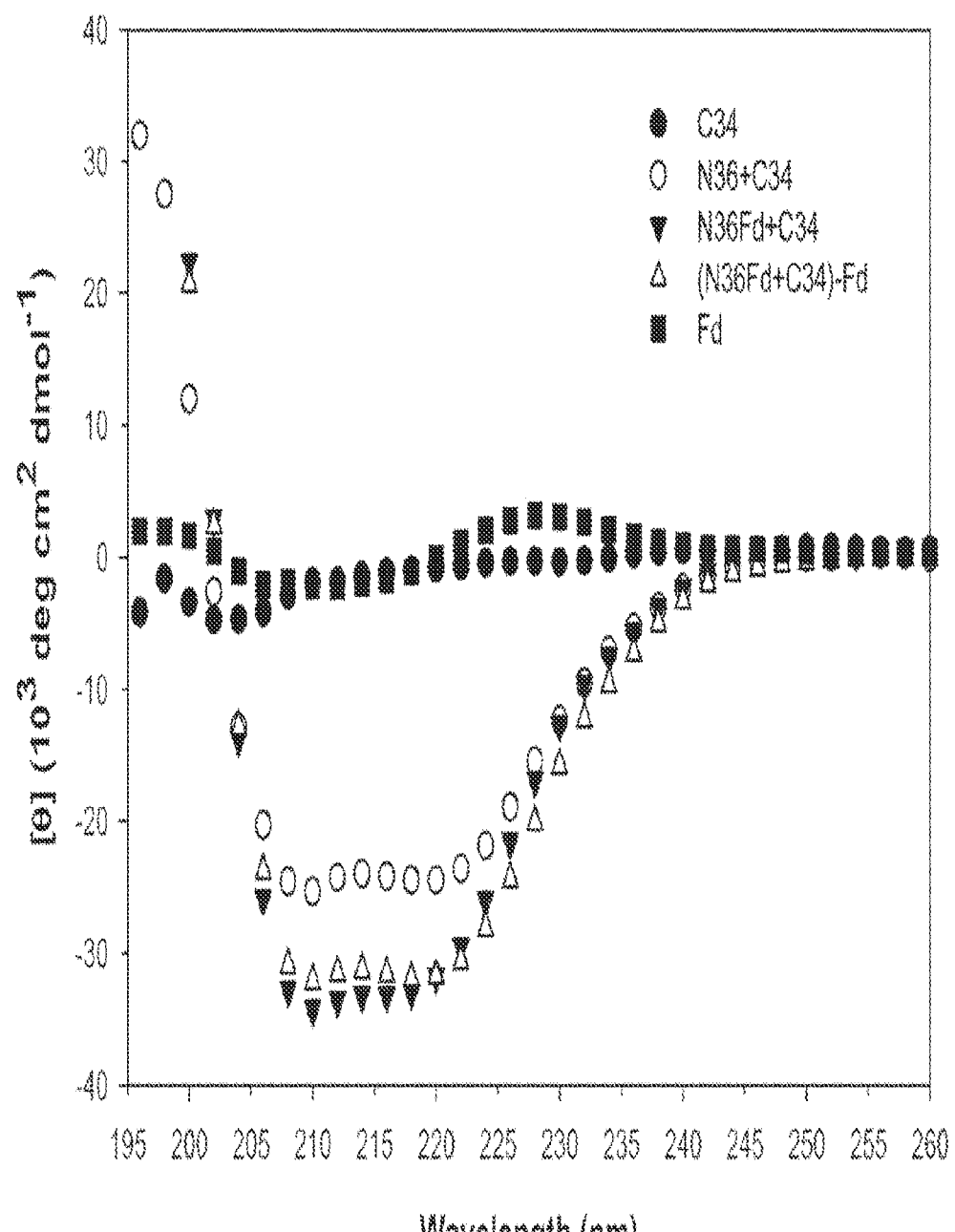
FIG. 8 illustrates CD spectroscopy analysis of the secondary structures of the complexes of C34 with N36 and N36Fd, respectively. The spectra of (N36Fd+C34)-Fd was calculated by subtracting the spectra of Fd peptide from those of N36Fd+C34.
Figure 9:
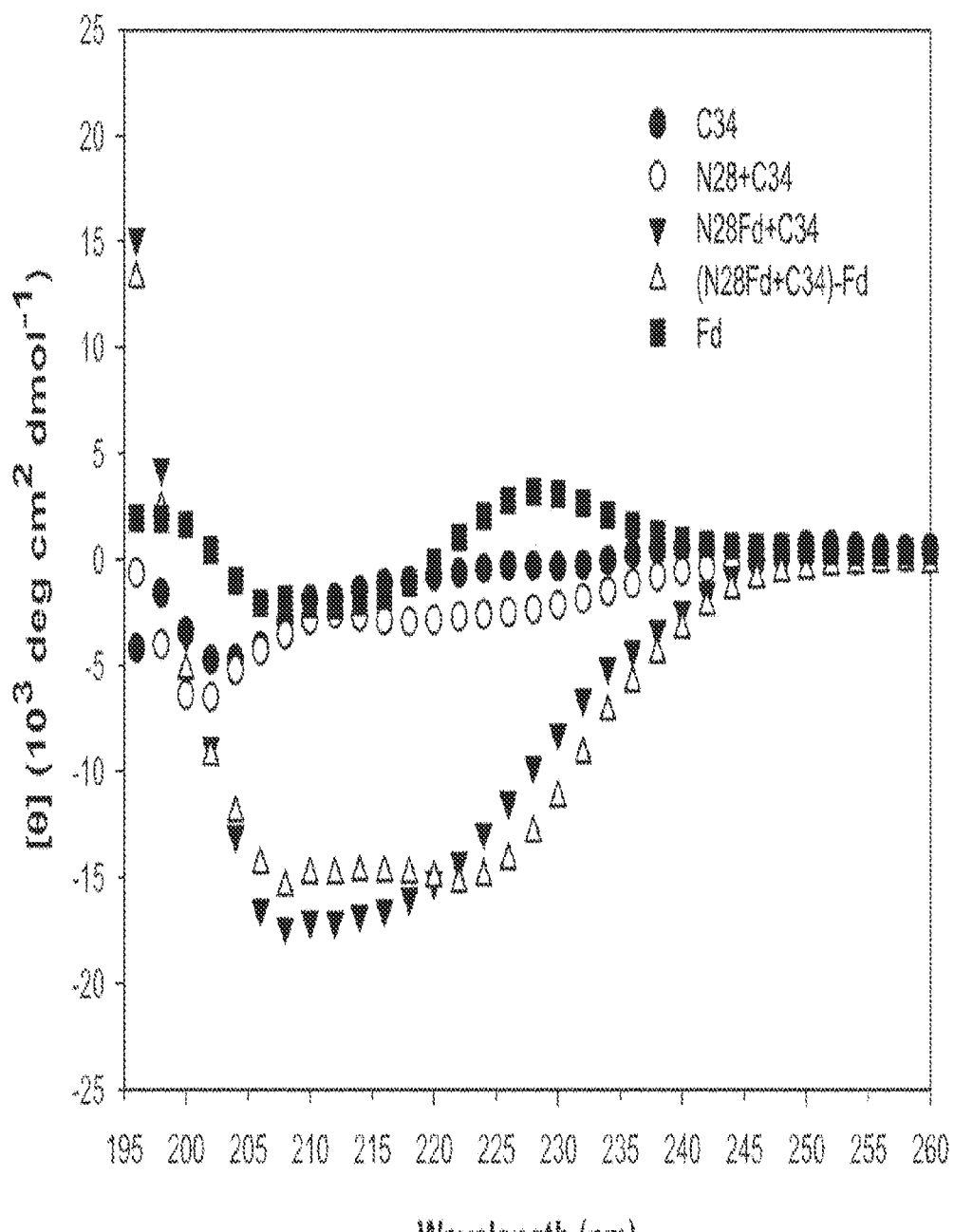
FIG. 9 illustrates CD spectroscopy analysis of the secondary structures of the complexes of C34 with N28 and N28Fd, respectively. The spectra of (N28Fd+C34)-Fd was calculated by subtracting the spectra of Fd peptide from those of N28Fd+C34.

CD spectroscopy was used to study the interaction of N36Fd or N28Fd trimers with C-peptides. When the molar ratio of N36Fd and C34 was 1:1, N36Fd interacted with C34 to form a complex that had significantly increased α-helicity (92.6% after subtracting the spectra of Fd) in comparison with N36+C34 (71.5% α-helicity) (FIG. 8). The $T_m$ value of N36Fd trimer+C34 (80.9° C.) is 15 degrees higher than that of N36+C34 (65.5° C.). Notably, free N28 peptide could not form a complex with C34, but fusion with Fd promoted N28 to bind to C34 and fold into a conformation with 46.3% α-helicity (FIG. 9) and 62.2° C. of $T_m$ value. This suggests that the Fd-based NHR-trimer is more effective than free N-peptide to interact with C-peptides to form stable 6-HB.

EXAMPLE 5

N36Fd and N28Fd are Much More Potent than N36 and N28, Respectively, in Inhibiting HIV-1-Mediated Cell-Cell Fusion The inhibitory activities of N36Fd and N36 on HIV-1-induced cell-cell fusion were determined using a dye transfer assay. Briefly, H9/HIV-1$_{IIIB}$ cells were pre-labeled with a fluorescent dye, Calcein AM (Molecular Probes, Inc., Eugene, Oreg.), and incubated with a testing compound at a graded concentration at 37° C. for 30 min in a 96-well cell culture plate. Then the CD4+ MT-2 cells were added to the H9/HIV-1$_{IIIB}$ cells at a ratio of 10:1, followed by incubation at 37° C. for 2 hrs. The fused and unfused Calcein-labeled HIV-1-infected cells were counted under an inverted fluorescence microscope (Zeiss, Germany) with an eyepiece micrometer disc. The percent inhibition of cell fusion by a compound and the $EC_{50}$ and $EC_{90}$ values were calculated using the software CalcuSyn.

Figure 10:
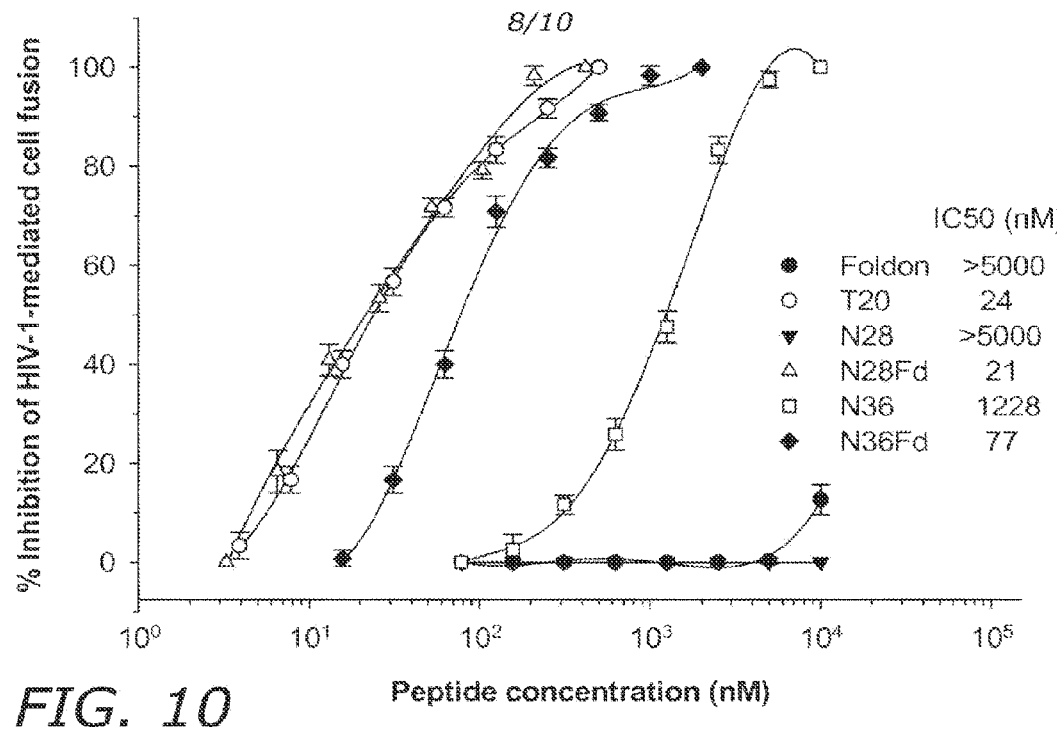
FIG. 10 illustrates the inhibitory activity of N36, N28, N36Fd and N28Fd, respectively, on the HIV-1$_{IIIB}$-mediated cell-cell fusion. The C-peptide T20 and Fd peptide were included as a control. The IC$_{50}$ value of each peptide was shown in the figure.

As shown in FIG. 10, N36Fd trimer was about 15-fold more potent than N36, while N28Fd trimer was >138-fold more effective than N28 in inhibiting HIV-1-induced cell-cell fusion. The N28Fd trimer displayed an $IC_{50}$ value of 21 nM, which is as potent as the clinically used peptide anti-HIV-1 drug T20 (Enfuvirtide, $IC_{50}$=24 nM). As a control, Fd peptide alone showed no inhibitory activity at the concentration up to 5,000 nM. This result suggests that the Fd-fused N-peptides function as potent HIV-1 fusion inhibitors.

EXAMPLE 6

Figure 11:
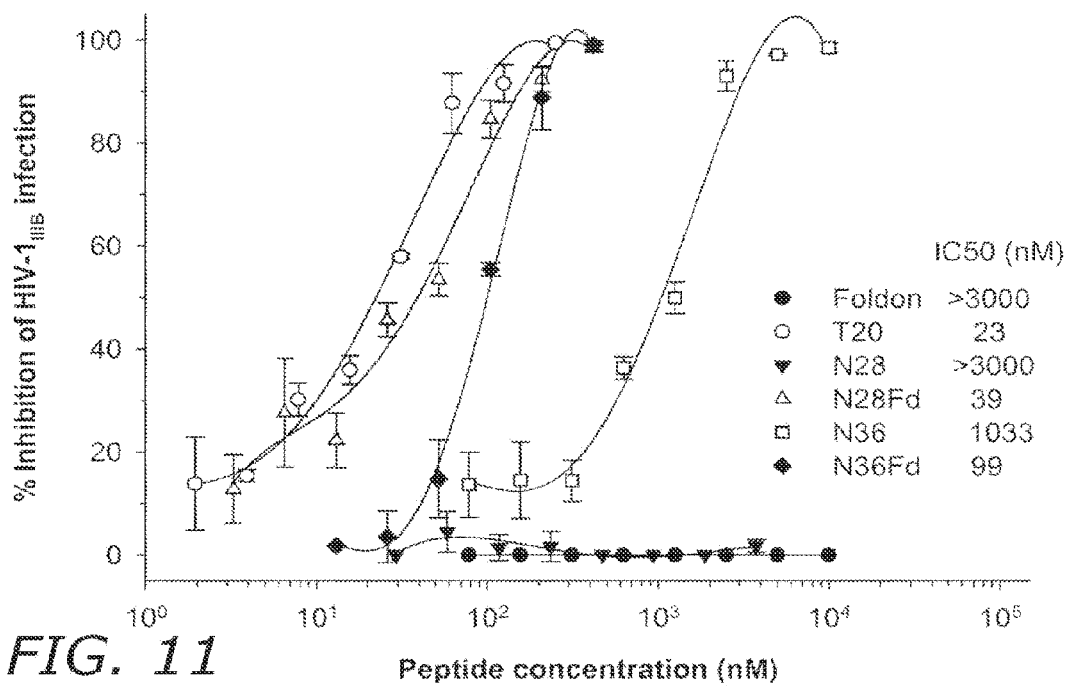
FIG. 11 illustrates the inhibitory activity of N36, N28, N36Fd and N28Fd, respectively, on infection by the HIV-1$_{IIIB}$ (subtype B, X4). The C-peptide T20 and Fd peptide were included as a control. The IC$_{50}$ value of each peptide was shown in the figure.

N36Fd and N28Fd are Much More Effective than N36 and N28, Respectively, in Inhibiting Infection by HIV-1 X4 Virus The inhibitory activity of N36Fd and N36 on HIV-1 replication was determined as previously described. In brief, 1×10⁴ MT-2 cells were infected with HIV-1$_{IIIB}$ in 200 µl RPMI 1640 medium containing 10% FBS in the presence or absence of testing compounds at graded concentrations overnight. Then the culture supernatants were removed and fresh media containing no testing compounds were added. On the fourth day post-infection, 100 µl of culture supernatants were collected from each well, mixed with equal volumes of 5% Triton X-100 and assayed for p24 antigen, which was quantitated by ELISA. Briefly, wells of polystyrene plates (Immulon 1B, Dynex Technology, Chantilly, Va.) were coated with HIV immunoglobulin (HIVIG), which was prepared from plasma of HIV-seropositive donors with high neutralizing titers against HIV-1$_{IIIB}$, in 0.085 M carbonate-bicarbonate buffer (pH 9.6) at 4° C. overnight, followed by washes with washing buffer (0.01M PBS containing 0.05% Tween-20) and blocking with PBS containing 1% dry fat-free milk (Bio-Rad Inc., Hercules, Calif.). Virus lysates were added to the wells and incubated at 37° C. for 1 h. After extensive washes, anti-p24 mAb (183-12H-5C), biotin labeled anti-mouse IgG1 (Santa Cruz Biotech., Santa Cruz, Calif.), streptavidin-labeled horseradish peroxidase (Zymed, S. San Francisco, Calif.), and the substrate 3,3',5,5'-tetramethylbenzidine (Sigma Chemical Co.) were added sequentially. Reactions were terminated by addition of 1N $H_2SO_4$. Absorbance at 450 nm was recorded in an ELISA reader (Ultra 386, TECAN, Research Triangle Park, NC). Recombinant protein p24 purchased from US Biological (Swampscott, Mass.) was included for establishing standard dose response curves. Each sample was tested in triplicate. The percentage of inhibition of p24 production was calculated as previously described. As shown in FIG. 11, both N36Fd and N28Fd trimers could effectively inhibit HIV-1$_{IIIB}$ replication with $IC_{50}$ values of 99 nM and 39 nM, respectively. N36 peptide exhibited moderate inhibitory activity ($IC_{50}$=1,033 nM), while Fd and N28 peptides showed no inhibitory activity at a concentration as high as 3,000 nM (FIG. 6A). N28Fd displayed higher antiviral activity than N36Fd.

EXAMPLE 7

N36Fd and N28Fd are Much More Effective than N36 and N28, Respectively, in Inhibiting Infection by HIV-1 R5 Viruses For inhibition of infection by the M-tropic HIV-1 strain Bal (subtype B, R5), 100 µl of TZM-bl cells (1×10⁵/ml) were pre-cultured overnight and infected with Bal at 100 TCID50 (50% tissue culture infective dose) in the presence or absence of the test peptide overnight. The cells were harvested and lysed on the fourth day post-infection with 50p1 of lysing reagent. The luciferase activity was analyzed using a luciferase kit (Promega, Madison, Wis.) and a luminometer (Ultra 386) according to the manufacturer's instructions. The percent inhibition of luciferase activity was calculated.

For inhibition of infection by the primary HIV-1 isolate 93IN101 (subtype C, R5), the peripheral blood mononuclear cells (PBMCs) were isolated from the blood of healthy donors using a standard density gradient (Histopaque-1077, Sigma) centrifugation. After incubation at 37° C. for 2 h, the nonadherent cells were collected and resuspended at 5×10⁵/ml in RPMI medium 1640 containing 10% FBS, 5 µg of phytohemagglutinin (PHA)/ml, and 100 U of interleukin-2/ml, followed by incubation at 37° C. for 3 days. The PHA-stimulated cells were infected with the primary HIV-1 isolate at a multiplicity of infection (MOI) of 0.01 in the absence or presence of N-Fd peptides at graded concentrations. The supernatants were collected on the 7th day post-infection and tested for p24 antigen by ELISA.

Figure 12:
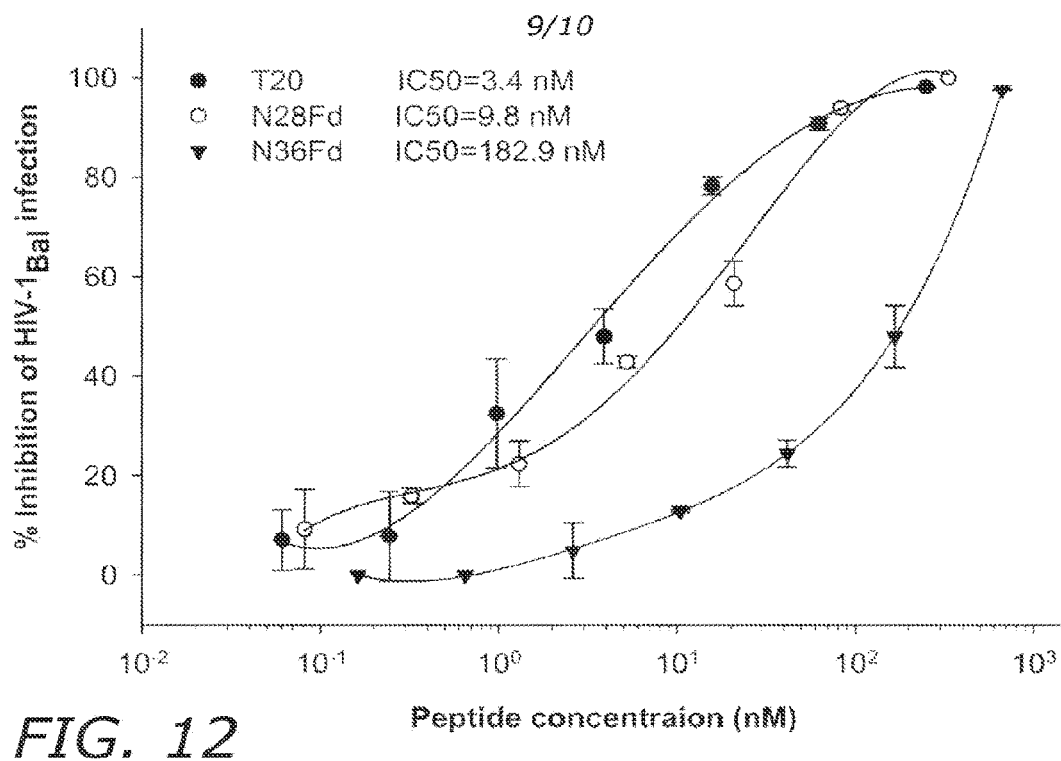
FIG. 12 illustrates the inhibitory activity of N36Fd and N28Fd, respectively, on infection by the HIV-1$_{Bal}$ (subtype B, R5). The C-peptide T20 and Fd peptide were included as a control. The IC$_{50}$ value of each peptide was shown in the figure.
Figure 13:
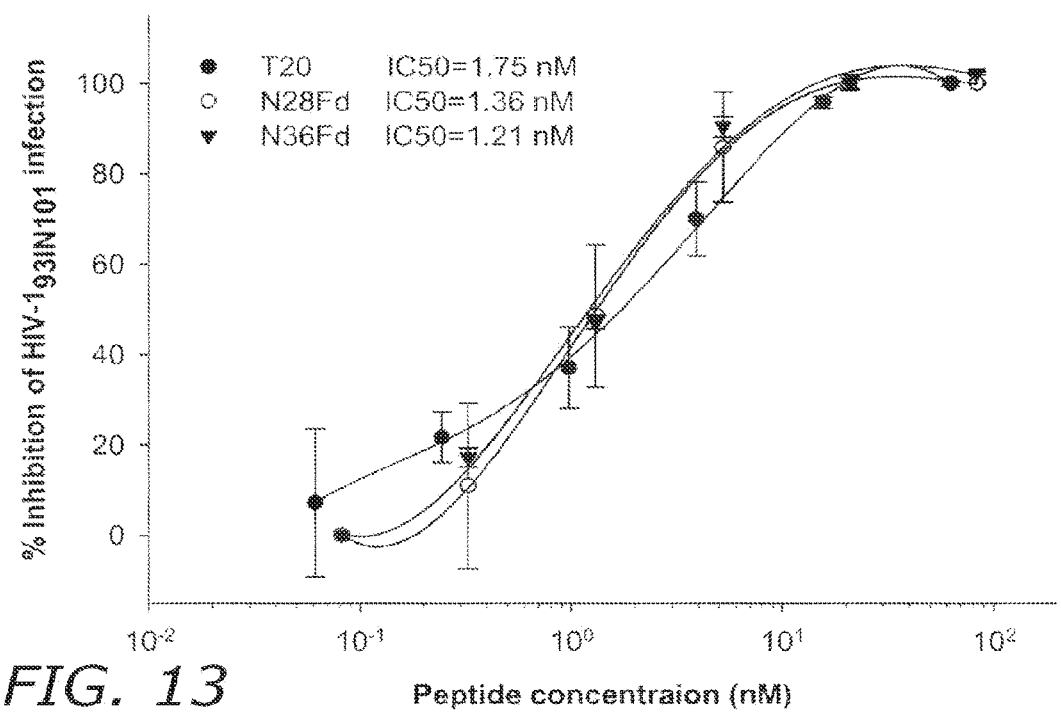
FIG. 13 illustrates the inhibitory activity of N36Fd and N28Fd, respectively, on infection by the HIV-1$_{93IN101}$ (subtype C, R5). The C-peptide T20 and Fd peptide were included as a control. The IC$_{50}$ value of each peptide was shown in the figure.

Both N36Fd and N28Fd trimers were effective against primary HIV-1 isolates using the coreceptor CCR5 (R5). N28Fd trimer blocked the infection by HIV-1 Bal (subtype B, R5) with an $IC_{50}$ of 9.8 nM (FIG. 12). N36Fd trimer had lower antiviral activity against Bal, with an $IC_{50}$ of 182.9 nM. Both N36Fd and N28Fd trimers displayed low-nanomolar inhibitory activity against the infection by HIV-1 93IN101 (subtype C, R5). The $IC_{50}$ values were 1.36 nM for the N36Fd trimer and 1.27 nM for the N28Fd trimer (FIG. 13). For comparison, T20 showed $IC_{50}$ values of 3.4 nM against Bal and 1.75 nM against 93IN101 in these two assays. These results suggest that N36Fd and N28Fd trimers, like T20, have a broad spectrum antiviral activity against HIV-1, irrespective of coreceptor usage.

EXAMPLE 8

N36Fd and N28Fd Trimers Exhibited Highly Potent Anti-HIV-1 Activities Against T20-Resistant Variants Mutations in the NHR region of HIV-1 virus NL4-3 cause genetic resistance to T20. The inhibitory activity of N36Fd and N28Fd trimers on the replication of T20-resistant strains was determined using p24 assay as described above. As shown in Table 1, T20 could potently inhibit the T20-sensitive strain HIV-$1_{NL4\text{-}3(36G)\ N42S}$ ($IC_{50}$=30 nM), but it was much less effective against the T20-resistant strains HIV-$1_{NL4\text{-}3(36G)\ N42T/N43K}$ ($IC_{50}$=374 nM), HIV-$1_{NL4\text{-}3(36G)\ V38E/N42S}$ ($IC_{50}$=1,390 nM), and HIV-$1_{NL4\text{-}3(36G)\ V38A/N42D}$ ($IC_{50}$=2,297 nM). However, N36Fd and N28Fd trimers had similar high potency against both T20-resistant and sensitive strains ($IC_{50}$=27~59 nM).

previously described. In brief, 50 μl of sample was coated onto wells of a 96-well polystyrene plate, followed by addition of rabbit antibodies directed against the HIV-1 gp41 N- and C-peptide mixture for binding N28Fd (at 1:400 dilution) and T20 (at 1:2000 dilution), respectively. Then, biotin-labeled goat anti-rabbit IgG (Sigma), streptavidin-labeled horseradish peroxidase (SA-HRP; Zymed), and the substrate 3,3',5,5'-tetramethylbenzidine (TMB; Sigma) were added sequentially. The absorbance at 450 nm (A450) was measured with an automatic enzyme-linked immunosorbent assay (ELISA) reader (Ultra 384). The remaining antiviral activity in the supernatants against HIV-$1_{IIIB}$ infection was determined as described above. In both assays, the untreated N28Fd and T20 were used as controls.

Figure 14:
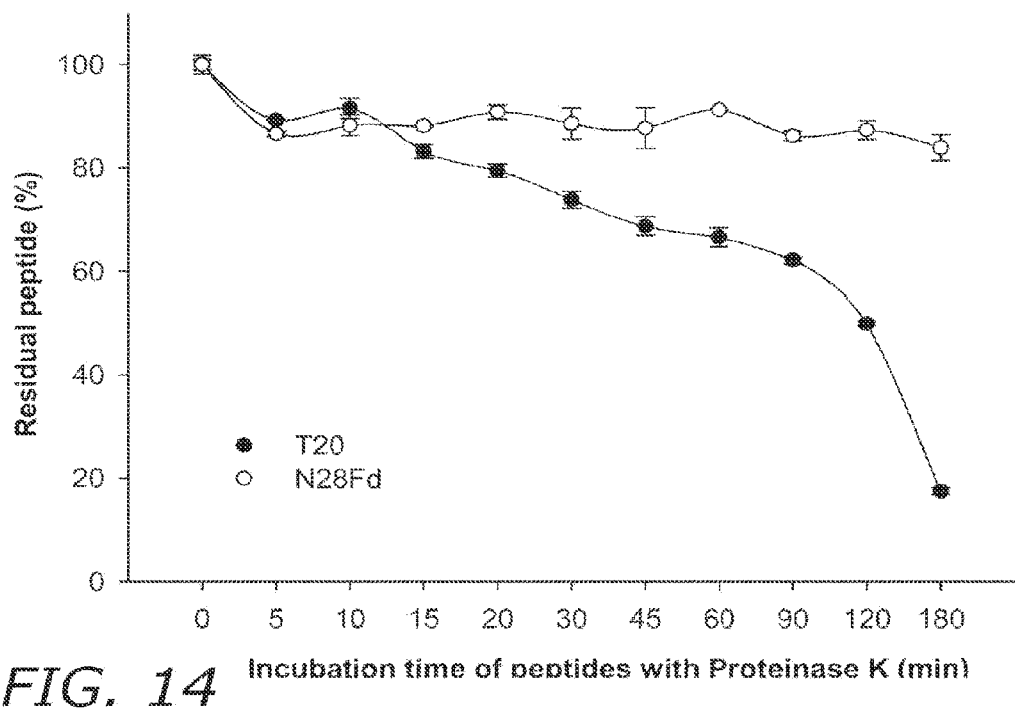
FIG. 14 illustrates the residual amount of N28Fd or T20 detected by a direct ELISA after digestion by proteinase K for different times.
Figure 15:
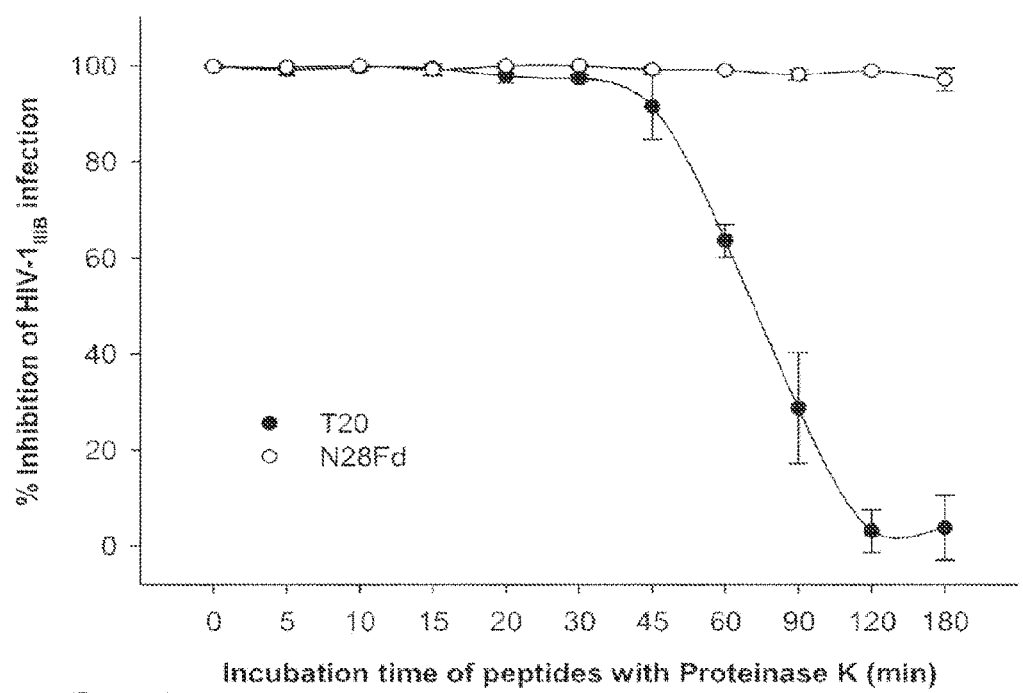
FIG. 15 illustrates the remaining antiviral potency of N28Fd or T20 tested by inhibition of HIV-1$_{IIIB}$ assay after digestion by proteinase K for different times.

After treatment with 1 μU/ml Proteinase K in PBS for 3 hrs, the N28Fd trimer maintained 84% of the original amount detected by ELISA and 97% of the original antiviral activity against HIV-$1_{IIIB}$ infection (FIGS. 14 and 15). Under the same conditions, T20 retained only 17% of the original activity (FIG. 14) and completely lost its anti-HIV-1 activity after 3-hour treatment with Proteinase K (FIG. 15). These results suggest that the N28Fd trimer is considerably more resistant to Proteinase K than T20.

Compounds useful in accordance with the present invention include pharmaceutically acceptable salt forms, prodrugs and stereoisomers thereof.

TABLE 2

| SEQ ID NO: (construct) | Amino Acid Sequence |
|---|---|
| 1 (N36Fd1) | SGIVQQQNNLLRAIEAQQHLLQLTVWGIKQLQARILGYI PEAPRDGQAYVRKDGEWVLLSTFL |

TABLE 1

Inhibitory activity of N28Fd and N36Fd against infection by T20-resistant HIV-1 strains

| | | $IC_{50}$ (nM) | | |
|---|---|---|---|---|
| HIV-1 strain | Phenotype | T20 | N28Fd trimer | N36Fd trimer |
| HIV-$1_{NL4\text{-}3(36G)\ N42S}$ | T20-sensitive | 30.03 ± 12.88 | 26.95 ± 0.02 | 56.34 ± 9.24 |
| HIV-$1_{NL4\text{-}3(36G)\ N42T/N43K}$ | T20-resistant | 373.82 ± 25.65 | 30.56 ± 6.07 | 25.22 ± 4.68 |
| HIV-$1_{NL4\text{-}3(36G)\ V38E/N42S}$ | T20-resistant | 1389.85 ± 60.67 | 46.43 ± 4.49 | 45.32 ± 6.28 |
| HIV-$1_{NL4\text{-}3(36G)\ V38A/N42D}$ | T20-resistant | 2297.19 ± 326.23 | 29.03 ± 0.82 | 56.80 ± 6.40 |

EXAMPLE 9

N28Fd was Much More Resistant than T20 to Proteinase K Digestion

One of the principal disadvantages of the current gp41 CHR-based peptide drug T20 is its short half-life in vivo and high sensitivity to the proteolytic enzymes in blood. It is the non-binding hypothesis of the present inventors that the well-folded secondary conformation of N28Fd trimer might be resistant to proteolytic enzymes. Therefore, the stability of N28Fd trimer under the digestion of the broad-spectrum serine proteinase, Proteinase K, was determined. T20 was used as a control. Peptide (40 μg/ml) was incubated at 37° C. in PBS containing 1 μU/ml Proteinase K-Acrylic Beads (Sigma). Samples were collected at different times and centrifuged immediately. The supernatants were collected and stored at −20° C. before testing. The residual peptide concentration in each sample was then detected by ELISA as TABLE 2-continued

| SEQ ID NO: (construct) | Amino Acid Sequence |
|---|---|
| 2 (N46Fd1) | TLTVQARQLLSGIVQQQNNLLRAIEAQQHLLQLTVWGIK QLQARILGYIPEAPRDGQAYVRKDGEWVLLSTFL |
| 3 (N51Fd1) | QARQLLSGIVQQQNNLLRAIEAQQHLLQLTVWGIKQLQA RILAVERYLKQQGYIPEAPRDGQAYVRKDGEWVLLSTFL |
| 4 (N54Fd1) | STMGAASMTLTVQARQLLSGIVQQQNNLLRAIEAQQHLL QLTVWGIKQLQARILGYIPEAPRDGQAYVRKDGEWVLLS TFL |
| 5 (N60Fd1) | STMGAASMTLTVQARQLLSGIVQQQNNLLRAIEAQQHLL QLTVWGIKQLQARILAVERYLGYIPEAPRDGQAYVRKDG EVVVLLSTFL |
| 6 (FdN28Fd1) | IEAQQHLLQLTVWGIKQLQARILAVERYGYIPEAPRDGQ AYVRKDGEWVLLSTFL |

TABLE 2-continued

| SEQ ID NO: (construct) | Amino Acid Sequence |
|---|---|
| 7 (N17Fd1) | LLQLTVWGIKQLQARILGYIPEAPRDGQAYVRKDGEWVLLSTFL |
| 8 (N36Fd2) | SGIVQQQNNLLRAIEAQQHLLQLTVWGIKQLQARILGSGYIPEAPRDGQAYVRKDGEWVLLSTFL |
| 9 (N46Fd2) | TLTVQARQLLSGIVQQQNNLLRAIEAQQHLLQLTVWGIKQLQARILGSGYIPEAPRDGQAYVRKDGEWVLLSTFL |
| 10 (N51Fd2) | QARQLLSGIVQQQNNLLRAIEAQQHLLQLTVWGIKQLQARILAVERYLKQQGSGYIPEAPRDGQAYVRKDGEWVLLSTFL |
| 11 (N54Fd2) | STMGAASMTLTVQARQLLSGIVQQQNNLLRAIEAQQHLLQLTVWGIKQLQARILGSGYIPEAPRDGQAYVRKDGEWVLLSTFL |
| 12 (N60Fd2) | STMGAASMTLTVQARQLLSGIVQQQNNLLRAIEAQQHLLQLTVWGIKQLQARILAVERYLGSGYIPEAPRDGQAYVRKDGEWVLLSTFL |
| 13 (N28Fd2) | IEAQQHLLQLTVWGIKQLQARILAVERYGSGYIPEAPRDGQAYVRKDGEWVLLSTFL |
| 14 (N17Fd2) | LLQLTVWGIKQLQARILGSGYIPEAPRDGQAYVRKDGEWVLLSTFL |
| 15 (C14Fd1) | WMEWDREINNYTSLGYIPEAPRDGQAYVRKDGEWVLLSTFL |
| 16 (C21Fd1) | WMEWDREINNYTSLIHSLIEEGYIPEAPRDGQAYVRKDGEWVLLSTFL |
| 17 (C28Fd1) | WMEWDREINNYTSLIHSLIEESQNQQEKGYIPEAPRDGQAYVRKDGEWVLLSTFL |
| 18 (C34Fd1) | WMEWDREINNYTSLIHSLIEESQNQQEKNEQELLGYIPEAPRDGQAYVRKDGEWVLLSTFL |
| 19 (C36Fd1) | WMEWDREINNYTSLIHSLIEESQNQQEKNEQELLELGYIPEAPRDGQAYVRKDGEWVLLSTFL |
| 20 (C38Fd1) | TTWMEWDREINNYTSLIHSLIEESQNQQEKNEQELLELGYIPEAPRDGQAYVRKDGEWVLLSTFL |
| 21 (C46Fd1) | WMEWDREINNYTSLIHSLIEESQNQQEKNEQELLELDKWASLWNWFGYIPEAPRDGQAYVRKDGEWVLLSTFL |
| 22 (C14Fd2) | WMEWDREINNYTSLGSGYIPEAPRDGQAYVRKDGEWVLLSTFL |
| 23 (C21Fd2) | WMEWDREINNYTSLIHSLIEEGSGYIPEAPRDGQAYVRKDGEWVLLSTFL |
| 24 (C28Fd2) | WMEWDREINNYTSLIHSLIEESQNQQEKGSGYIPEAPRDGQAYVRKDGEWVLLSTFL |
| 25 (C34Fd2) | WMEWDREINNYTSLIHSLIEESQNQQEKNEQELLGSGYIPEAPRDGQAYVRKDGEWVLLSTFL |
| 26 (C36Fd2) | WMEWDREINNYTSLIHSLIEESQNQQEKNEQELLELGSGYIPEAPRDGQAYVRKDGEWVLLSTFL |
| 27 (C38Fd2) | TTWMEWDREINNYTSLIHSLIEESQNQQEKNEQELLELGSGYIPEAPRDGQAYVRKDGEWVLLSTFL |
| 28 (C46Fd2) | WMEWDREINNYTSLIHSLIEESQNQQEKNEQELLELDKWASLWNWFGSGYIPEAPRDGQAYVRKDGEWVLLSTFL |
| 29 (Fd1) | GYIPEAPRDGQAYVRKDGEWVLLSTFL |
| 30 (Fd2) | GSGYIPEAPRDGQAYVRKDGEWVLLSTFL |
| 31 (N36) | SGIVQQQNNLLRAIEAQQHLLQLTVWGIKQLQARIL |
| 32 (N28) | IEAQQHLLQLTVWGIKQLQARILAVERY |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of inhibiting the fusion of a human immunodeficiency virus (HIV) to a target cell comprising:
administering a trimeric polypeptide pharmaceutical composition to the target cells, wherein the composition comprises a trimeric polypeptide, wherein the trimeric polypeptide comprises three polypeptide monomers, each polypeptide monomer consisting of a fusion peptide consisting of the amino acid sequence of the N-terminal heptad repeat (NHR or HR1) of the transmembrane glycoprotein gp41 of HIV fused to a foldon trimerization motif, wherein the NHR is N28, and wherein the foldon trimerization motif sequence is fused to the C-terminus of the NHR; and
inhibiting fusion of the virus to the cell.

2. The method of claim 1, wherein said polypeptide monomer is produced by recombinant DNA technology.

3. The method of claim 1, wherein said polypeptide monomer comprises the amino acid sequence of SEQ ID NO. 6.

4. The method of claim 1, wherein said polypeptide monomer comprises the amino acid sequence of SEQ ID NO. 13.

* * * * *